United States Patent [19]

Serban et al.

[11] 4,248,618
[45] Feb. 3, 1981

[54] DERIVATIVES OF (PYRIMIDYLOXY)PHENOXY-ALKANECARBOXYLIC ACID AND HERBICIDAL COMPOSITIONS THEREOF

[75] Inventors: Alexander Serban, Doncaster; Richard B. Warner, Ringwood; Keith G. Watson, Box Hill, all of Australia

[73] Assignee: ICI Australia Limited, Melbourne, Australia

[21] Appl. No.: 899,395

[22] Filed: Apr. 24, 1978

[30] Foreign Application Priority Data

May 6, 1977 [AU] Australia .................. PD0012

[51] Int. Cl.³ .......................... C07D 239/24
[52] U.S. Cl. .......................... 71/92; 544/315; 544/316; 544/317; 544/318; 544/123; 544/122
[58] Field of Search ............... 544/318, 317, 315, 316; 71/92

[56] References Cited

U.S. PATENT DOCUMENTS

| | | | |
|---|---|---|---|
| 3,502,673 | 3/1970 | Hepworth et al. | 544/315 |
| 3,557,112 | 1/1971 | D'Amico et al. | 544/315 |
| 3,652,257 | 3/1972 | Jojima et al. | 71/92 |
| 4,001,234 | 1/1977 | Johnston | 544/316 |

Primary Examiner—Nicholas S. Rizzo
Attorney, Agent, or Firm—Cushman, Darby & Cushman

[57] ABSTRACT

A compound of general formula I:

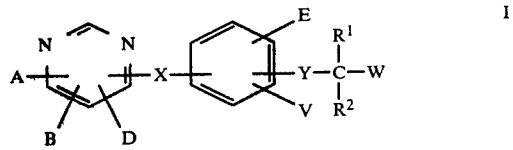

wherein A, B, D, E, and V are independently chosen from hydrogen, halogen, nitro, cyano, thiocyano, amino, alkyl, alkoxy, alkylthio, alkenyl, cycloalkyl, carbalkoxy, phenyl, phenoxy or phenylthio; $R^1$ and $R^2$ are independently hydrogen, alkyl, alkenyl, alkanoyl, or $R^1$ and $R^2$ together are alkylidene; W is carboxy or a functional derivative thereof or $CH_2Z$ wherein Z is halogen, hydroxy, alkoxy, alkylthio, formyl or amino; and X and Y are oxygen or sulfur.

28 Claims, No Drawings

DERIVATIVES OF (PYRIMIDYLOXY)PHENOXY-ALKANECARBOXYLIC ACID AND HERBICIDAL COMPOSITIONS THEREOF

This invention relates to organic compounds having biological activity and in particular to organic compounds having herbicidal properties, and to herbicidal compositions and processes utilizing such compounds.

We have found that certain novel (pyrimidyloxy)-phenoxyalkanecarboxylic acids and the derivatives thereof exhibit biological activity and in particular herbicidal activity.

Accordingly we provide a compound of general formula I:

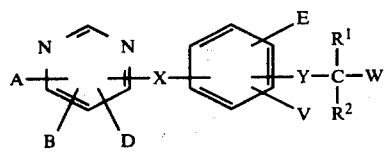

or an optical isomer thereof or a salt therefrom wherein:
A, B, D, E and V are independently chosen from the group consisting of hydrogen, halogen, nitro, cyano, thiocyano, amino optionally substituted with one or two $C_1$ to $C_6$ alkyl groups, $C_1$ to $C_6$ alkyl optionally substituted with one or more halogen atoms, $C_1$ to $C_6$ alkoxy, $C_1$ to $C_6$ alkylthio, $C_2$ to $C_6$ alkenyl, $C_3$ to $C_7$ cycloalkyl, carbalkoxy wherein alkoxy is a $C_1$ to $C_6$ alkoxy group, and the groups phenyl, phenoxy or phenylthio wherein in each group the phenyl ring is optionally substituted with one or more substituents chosen from halogen, trifluoromethyl $C_1$ to $C_6$ alkyl, $C_1$ to $C_6$ alkoxy, nitro and cyano;

$R^1$ and $R^2$ are independently chosen from the group consisting of hydrogen, $C_1$ to $C_6$ alkyl, $C_2$ to $C_6$ alkenyl, $C_2$ to $C_6$ alkoxyalkyl, $C_1$ to $C_4$ haloalkyl, acetyl and propionyl or $R^1$ and $R^2$ together may form a methylene, ethylidene, propylidene or isopropylidene group;

W is chosen from the group consisting of cyano, thiocarbamoyl,

and $CH_2Z$ wherein: G is chosen from the group consisting of hydroxy, mercapto, $C_1$ to $C_{10}$ alkoxy optionally substituted with halogen, hydroxy or $C_1$ to $C_6$ alkoxy, $C_1$ to $C_6$ alkylthio, $C_2$ to $C_{10}$ alkenyloxy, $C_2$ to $C_{10}$ alkynyloxy, $C_2$ to $C_{10}$ alkenylthio, $C_3$ to $C_7$ cycloalkoxy optionally substituted with one or two $C_1$ to $C_4$ alkyl groups, the groups phenoxy, phenylthio, benzyloxy and benzylthio each optionally substituted in the phenyl ring with one or two substituents chosen from halogen; nitro, $C_1$ to $C_6$ alkyl and $C_1$ to $C_6$ alkoxy, the group OM wherein M is the cation of an inorganic or organic base, and the groups -$NR^3R^4$ and -NH-$NR^3R^4$ wherein $R^3$ and $R^4$ are independently chosen from the group consisting of hydrogen, $C_1$ to $C_6$ alkyl optionally substituted with halogen, hydroxy, carboxy or $C_1$ to $C_6$ alkoxycarbonyl, $C_2$ to $C_6$ alkenyl, $C_5$ to $C_7$ cycloalkyl, thienylmethyl, the groups phenyl or benzyl optionally substituted on the phenyl ring with one or two substituents chosen from halogen, $C_1$ to $C_6$ alkyl, $C_1$ to $C_6$ alkoxy, or $R^3$ and $R^4$ together form a heterocyclic ring; and Z is chosen from halogen, hydroxy, mercapto, $C_1$ to $C_{10}$ alkoxy optionally substituted with halogen, hydroxy or $C_1$ to $C_6$ alkoxy, $C_1$ to $C_{10}$ alkylthio optionally substituted with halogen, hydroxy or $C_1$ to $C_6$ alkoxy, formyl, and the group $NR^3R^4$ wherein $R^3$ and $R^4$ are as hereinbefore defined; and X and Y are independently chosen from oxygen and sulfur.

The compounds of general formula I wherein $R^1$ and $R^2$ are not the same, are optically active and the present invention also includes the individual stero isomers of such compounds, and mixtures of those stereo isomers in addition to the racemic mixture of stereo isomers.

Preferred A, B and D are hydrogen, $C_1$ to $C_6$ alkyl, $C_1$ to $C_6$ alkoxycarbonyl, halogen, cyano, $C_1$ to $C_6$ alkoxy, $C_1$ to $C_6$ haloalkyl, phenyl optionally substituted with halogen or nitro and phenoxy optionally substituted with halogen.

Preferred E and V are hydrogen, halogen, nitro, $C_1$ to $C_6$ alkyl and $C_1$ to $C_6$ haloalkyl.

Preferred $R^1$ is hydrogen or $C_1$ to $C_6$ alkyl, preferred $R^2$ is hydrogen or methyl.

Preferred W are the groups

wherein G is chosen from the group consisting of hydroxy; $C_1$ to $C_{10}$ alkoxy optionally substituted with halogen, phenyl or $C_1$ to $C_6$ alkoxy; $C_1$ to $C_{10}$ alkylthio optionally substituted with phenyl; $C_2$ to $C_{10}$ alkenyloxy; $C_2$ to $C_{10}$ alkynyloxy; phenoxy optionally substituted with one or two nitro groups; cyclohexyloxy; amino optionally substituted with one or more substituents chosen from $C_1$ to $C_6$ alkyl, phenyl, thienylmethyl; morpholino; and OM wherein M is an alkali metal ion an alkaline earth metal ion or an ammonium ion $HN^{\oplus}R^5R^6R^7$ wherein $R^5$, $R^6$ and $R^7$ are independently chosen from the group consisting of hydrogen, $C_1$ to $C_6$ alkyl, $C_1$ to $C_6$ hydroxyalkyl, phenyl and benzyl; and the group -$CH_2Z$ wherein Z is chosen from the group consisting of halogen, hydroxy, mercapto, $C_1$ to $C_{10}$ alkoxy, amino optionally substituted with one or two substituents chosen from $C_1$ to $C_6$ alkyl and phenyl, and morpholino. More preferably W is the group

wherein G is chosen from the group consisting of hydroxy, $C_1$ to $C_{10}$ alkoxy optionally substituted with halogen or $C_1$ to $C_6$ alkoxy, $C_2$ to $C_{10}$ alkenyloxy, $C_2$ to $C_{10}$ alkynyloxy and cyclohexyloxy.

Preferred X and Y are oxygen. Examples of the compounds embraced by the invention include

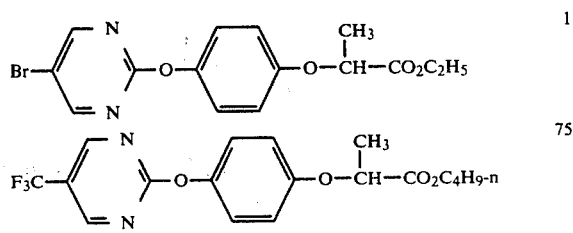

Specific examples of the compounds of the invention are: compounds of the formula XX wherein W is the group $$-\overset{O}{\underset{\|}{C}}-G,$$

detailed in Table 1; compounds of the formula XXI wherein W is the group $$-\overset{O}{\underset{\|}{C}}-G,$$

detailed in Table 2; compounds of the formula XXII wherein W is the group $$-\overset{O}{\underset{\|}{C}}-G,$$

detailed in Table 3; compounds of the formula XXIII wherein W is the group $$-\overset{O}{\underset{\|}{C}}-G,$$

detailed in Table 4; and compounds of the formula XXIV

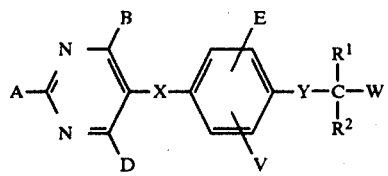

wherein W is the group

XXIV

detailed in Table 5.

TABLE 1

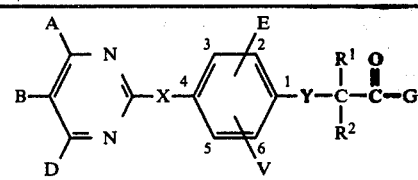

| Compound No | A | B | D | E | V | X | Y | R¹ | R² | G |
|---|---|---|---|---|---|---|---|---|---|---|
| 1 | H | Br | H | H | H | O | O | CH₃ | H | OC₂H₅ |
| 3 | H | Cl | H | H | H | O | O | H | H | OC₂H₅ |
| 11 | H | H | H | H | H | O | O | H | H | OC₂H₅ |
| 12 | H | H | H | H | H | O | O | CH₃ | H | OC₂H₅ |
| 13 | H | Cl | H | H | H | O | O | CH₃ | H | OC₂H₅ |
| 14 | H | Cl | H | H | H | O | O | CH₃ | H | OCH₃ |
| 15 | H | Br | H | H | H | O | O | CH₃ | H | OCH₃ |
| 16 | H | I | H | H | H | O | O | CH₃ | H | OC₂H₅ |
| 17 | CH₃ | H | CH₃ | H | H | O | O | CH₃ | H | OC₂H₅ |
| 18 | CH₃ | Br | CH₃ | H | H | O | O | CH₃ | H | OC₂H₅ |
| 19 | H | Br | H | 3-t-Bu | H | O | O | CH₃ | H | OC₂H₅ |
| 20 | CH₃ | Br | H | H | H | O | O | CH₃ | H | OC₂H₅ |
| 21 | H | Ph | H | H | H | O | O | CH₃ | H | OC₂H₅ |
| 22 | H | CN | H | H | H | O | O | CH₃ | H | OC₂H₅ |
| 23 | H | CO₂C₂H₅ | H | H | H | O | O | CH₃ | H | OCH₃ |
| 24 | H | Br | H | H | H | O | O | CH₃ | CH₃ | OC₂H₅ |
| 25 | H | Br | H | H | H | O | O | C₂H₅ | H | OC₂H₅ |
| 26 | H | Br | H | H | H | O | O | n-C₆H₁₃ | H | OC₂H₅ |
| 27 | H | Cl | H | H | H | O | O | CH₃ | CH₃ | OC₂H₅ |
| 28 | H | Br | H | H | H | O | O | CH₃ | H | OBu-n |
| 29 | H | CH₃ | H | H | H | O | O | CH₃ | H | OC₂H₅ |
| 30 | H | CH₃ | H | H | H | O | O | CH₃ | H | OH |
| 31 | CO₂Et | Cl | H | H | H | O | O | CH₃ | H | OC₂H₅ |
| 32 | OCH₃ | Br | H | H | H | O | O | CH₃ | H | OCH₃ |
| 33 | H | Br | H | 3-Cl | H | O | O | CH₃ | H | OC₂H₅ |
| 34 | H | Br | H | 2-Cl | H | O | O | CH₃ | H | OCH₃ |
| 35 | H | Br | H | 2-Cl | H | O | O | CH₃ | H | OC₂H₅ |
| 36 | H | Br | H | H | H | O | O | CH₃ | H | OCH₂CH=CH₂ |
| 37 | H | I | H | H | H | O | O | CH₃ | H | OCH₃ |
| 38 | H | Br | H | H | H | O | O | CH₃ | H | OCH₂C≡CH |
| 39 | H | 4-Cl—C₆H₄ | H | H | H | O | O | CH₃ | H | OCH₃ |
| 40 | H | 4-O₂N—C₆H₄ | H | H | H | O | O | CH₃ | H | OCH₃ |
| 41 | H | Br | H | H | H | O | O | CH₃ | H | N(C₂H₅)₂ |
| 42 | H | Cl | H | H | H | S | O | CH₃ | H | OC₂H₅ |
| 43 | H | Br | H | H | H | O | O | CH₃ | H | OC(CCl₃)(CH₃)₂ |
| 44 | H | Cl | H | 3-Cl | H | O | O | CH₃ | H | OCH₃ |
| 45 | H | Cl | H | 2-NO₂ | H | O | O | CH₃ | H | OC₂H₅ |
| 46 | H | Cl | H | H | H | O | S | CH₃ | H | OCH₃ |
| 47 | H | Cl | H | 2-Cl | H | O | O | CH₃ | H | OCH₃ |
| 48 | H | Cl | H | 3-Cl | H | O | O | CH₃ | H | OCH₃ |
| 49 | H | F | H | H | H | O | O | CH₃ | H | OCH₃ |
| 50 | H | I | H | 2-Cl | H | O | O | CH₃ | H | OCH₃ |
| 51 | H | Cl | H | 2-Cl | H | O | O | CH₃ | H | OH |
| 52 | H | C₂H₅O | H | H | H | O | O | CH₃ | H | OH |
| 53 | H | Cl | H | 2-CF₃ | H | O | O | CH₃ | H | OC₂H₅ |
| 54 | H | Br | H | H | H | O | O | CH₃ | H | NH—CH₂-(2-thienyl) |
| 55 | H | Br | H | H | H | O | O | CH₃ | H | —N(morpholino) |
| 56 | H | Br | H | H | H | O | O | CH₃ | H | —NHPh |
| 57 | H | Br | H | H | H | O | O | CH₃ | H | O—C₆H₄—NO₂-p |
| 58 | H | Br | H | H | H | O | O | CH₃ | H | OCH₂C₆H₅ |
| 59 | H | Br | H | H | H | O | O | CH₃ | H | SCH₂—CH=CH₂ |
| 60 | H | Br | H | H | H | O | O | CH₃ | H | SCH₂C₆H₅ |
| 61 | Cl | H | H | H | H | O | O | CH₃ | H | OCH₃ |

TABLE 1-continued

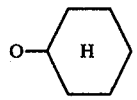

| Compound No | A | B | D | E | V | X | Y | R¹ | R² | G |
|---|---|---|---|---|---|---|---|---|---|---|
| 62 | H | Br | H | H | H | O | O | $CH_3$ | H | OH |
| 63 | H | Br | H | H | H | O | O | $CH_3$ | H | $OC_3H_7$-n |
| 64 | H | Br | H | H | H | O | O | $CH_3$ | H | $OCH(CH_3)_2$ |
| 65 | H | Br | H | H | H | O | O | $CH_3$ | H | $OCH_2CH(CH_3)_2$ |
| 66 | H | Br | H | H | H | O | O | $CH_3$ | H | $OCH(CH_3)C_2H_5$ |
| 67 | H | Br | H | H | H | O | O | $CH_3$ | H | $OC_5H_{11}$-n |
| 68 | H | Br | H | H | H | O | O | $CH_3$ | H | $OCH(CH_3)CH_2CH(CH_3)_2$ |
| 69 | H | Br | H | H | H | O | O | $CH_3$ | H | O-cyclohexyl |
| 70 | H | Br | H | H | H | O | O | $CH_3$ | H | $OCH_2CH(C_2H_5)C_4H_9$ |
| 71 | H | Br | H | H | H | O | O | $CH_3$ | H | $OCH_2CH_2OCH_3$ |
| 72 | H | Br | H | H | H | O | O | $CH_3$ | H | $OC_8H_{17}$-n |
| 73 | H | $CF_3$ | H | H | H | O | O | $CH_3$ | H | $OCH_3$ |
| 74 | H | $CF_3$ | H | H | H | O | O | $CH_3$ | H | $OC_2H_5$ |
| 75 | H | $CF_3$ | H | H | H | O | O | $CH_3$ | H | $OC_4H_9$-n |
| 94 | H | 3-$ClC_6H_4$—O | H | H | H | O | O | $CH_3$ | H | $OCH_3$ |

TABLE 2

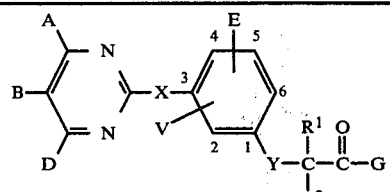

| Compound No | A | B | D | E | V | X | Y | R¹ | R² | G |
|---|---|---|---|---|---|---|---|---|---|---|
| 76 | H | Cl | H | H | H | O | O | $CH_3$ | H | $OCH_3$ |
| 77 | H | Cl | H | 6-$NO_2$ | H | O | O | $CH_3$ | H | $OC_2H_5$ |
| 78 | $CH_3$ | H | $CH_3$ | H | H | O | O | $CH_3$ | H | $OC_2H_5$ |
| 79 | $CH_3$ | H | $CH_3$ | H | H | O | O | H | H | $OC_2H_5$ |

TABLE 4

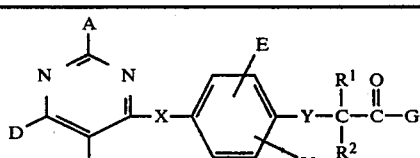

| Compound No | A | B | D | E | V | X | Y | R¹ | R² | G |
|---|---|---|---|---|---|---|---|---|---|---|
| 86 | $CH_3$ | H | $CH_3$ | H | H | O | O | $CH_3$ | H | $OC_2H_5$ |
| 87 | Cl | H | H | H | H | O | O | $CH_3$ | H | $OC_2H_5$ |
| 88 | H | H | Cl | H | H | O | O | $CH_3$ | H | $OCH_3$ |
| 89 | H | H | H | H | H | O | O | $CH_3$ | H | $OCH_3$ |
| 90 | Cl | Br | H | H | H | O | O | $CH_3$ | H | $OCH_3$ |
| 91 | $N(CH_3)_2$ | Br | H | H | H | O | O | $CH_3$ | H | $OCH_3$ |
| 92 | Cl | H | $CH_3$ | H | H | O | O | $CH_3$ | H | $OCH_3$ |

TABLE 3

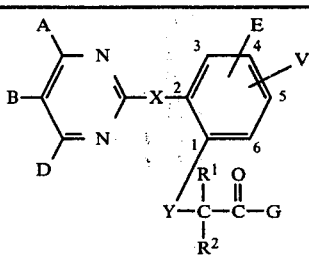

| Compound No | A | B | D | E | V | X | Y | R¹ | R² | G |
|---|---|---|---|---|---|---|---|---|---|---|
| 80 | H | Br | H | H | H | O | O | $CH_3$ | H | $OCH_3$ |
| 81 | H | Cl | H | H | H | O | O | $CH_3$ | H | $OCH_3$ |
| 82 | H | Cl | H | 5-Cl | H | O | O | $CH_3$ | H | $OCH_3$ |
| 83 | H | Cl | H | 5-$C_2H_5$ | H | O | O | $CH_3$ | H | $OCH_3$ |
| 84 | H | Cl | H | 4-Cl | H | O | O | $CH_3$ | H | $OCH_3$ |
| 85 | H | p-$NO_2$—$C_6H_4$ | H | H | H | O | O | $CH_3$ | H | $OCH_3$ |

TABLE 5

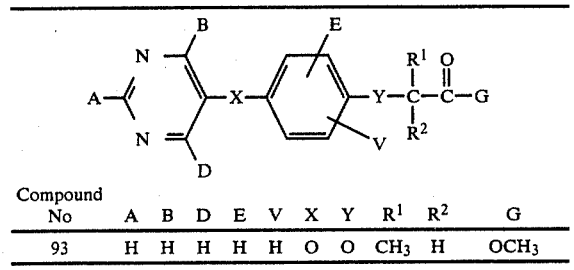

| Compound No | A | B | D | E | V | X | Y | $R^1$ | $R^2$ | G |
|---|---|---|---|---|---|---|---|---|---|---|
| 93 | H | H | H | H | H | O | O | $CH_3$ | H | $OCH_3$ |

The compounds of the invention may be prepared by a variety of methods and in a further aspect the invention provides methods for the preparation of the compounds of general formula I.

Compounds of formula Ia

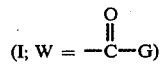

wherein G is not hydroxy may be prepared from the acid of formula Ib(I; W=—$CO_2H$) by any of the conventional methods known in the art for the conversion of a carboxylic acid to an acid salt, acid ester, acid amide or acid hydrazide (SCHEME A).

SCHEME A

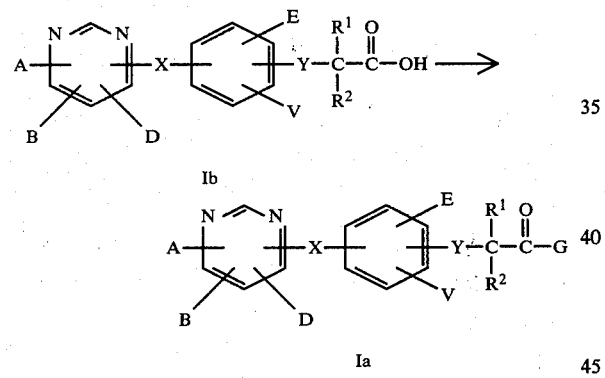

Compounds of formula Ic (I; W=—C≡N) may be prepared by any of the conventional methods known in the art for the conversion of an acid amide to the nitrile derivative of the acid (SCHEME B).

SCHEME B

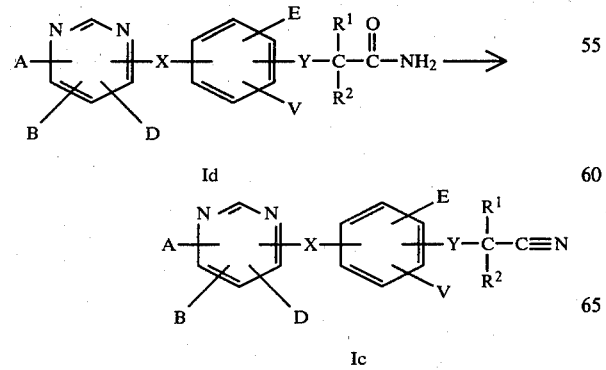

Compounds of formula Ie (I; W=—$CH_2OH$) may be prepared from the acid or acid esters of formula If (I;

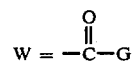

wherein G=OH or O-alkyl) by any of the conventional methods known in the art for the conversion of an acid or acid ester to an alcohol (e.g. LiAlH$_4$ reduction). (SCHEME C).

SCHEME C

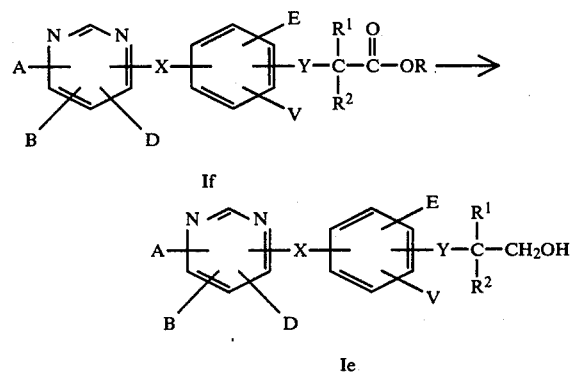

Alcohols of formula Ie (I; W=—$CH_2OH$) may be converted to alkyl halides (I; W=—$CH_2$—halogen) and ethers or thioethers (I; W=—$CH_2OR$ or —$CH_2SR$) by any of the conventional methods known in the art.

Amines of formula Ig (I; W=—$CH_2NR^3R^4$) may be prepared either from the alkyl halides (I; W=—$CH_2$ halogen) or by reduction of the amides

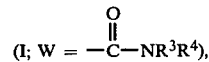

both conventional processes known in the art.

Compounds of general formula I wherein A, B, D, E, V, X, Y, $R^1$, $R^2$ and W are as hereinbefore defined may be prepared by the condensation of a phenoxy- or phenylthio- pyrimidine of formula IX with a compound of formula X wherein hal is chlorine, bromine or iodine, preferably in the presence of an alkalinie material; according to SCHEME D.

SCHEME D

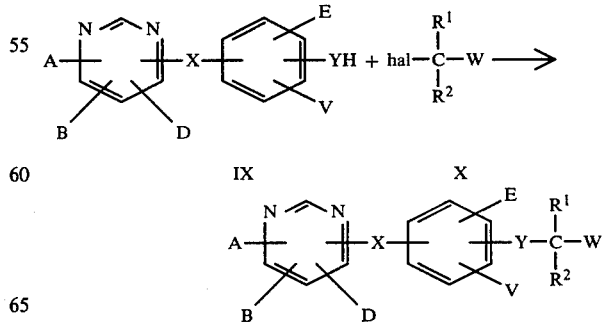

Compounds of the invention in which the group

[structure: X—⟨benzene with E,V⟩—Y—C(R¹)(R²)—W]

is substituted in the 2- or 4- positions of the pyrimidyl ring, for example, compounds of formula II, III, XX, XXI, XXII, and XXIII, may be prepared by:

(a) the condensation of the appropriate pyrimidine of formula V, wherein L is a good leaving group (for example, alkylsulfonyl, chlorine, bromine or iodine) with the appropriate phenol or thiophenol of formula VI, preferably in the presence of an alkaline material; according to SCHEME E

SCHEME E

[Scheme E: pyrimidine-L (V) + HX—aryl—Y—C(R¹)(R²)—W (VI) → pyrimidine—X—aryl—Y—C(R¹)(R²)—W (I)]

(b) the following steps in sequence:
  (i) the condensation of the appropriate pyrimidine of formula V, wherein L is a good leaving group (for example, alkylsulfonyl, chlorine, bromine or iodine) with the appropriate phenol or thiophenol of formula VII, wherein Q is hydroxy, mercapto, $C_1$ to $C_6$ alkoxy or $C_1$ to $C_6$ alkylthio, preferably in the presence of an alkaline material, to give a compound of formula VIII wherein Q is hydroxy, mercapto, $C_1$ to $C_6$ alkoxy or $C_1$ to $C_6$ alkylthio;
  (ii) the dealkylation of the compound of formula VIII prepared in step (i) above wherein Q is $C_1$ to $C_6$ alkoxy or $C_1$ to $C_6$ alkylthio to give a product of general formula IX; and
  (iii) the condensation of product of formula IX obtained in step (i) or step (ii) above with a compound of formula X according to the process described for SCHEME D above. (Steps (i) and (ii) are shown in SCHEME F).

SCHEME F

[Scheme F (i): pyrimidine-L (V) + HX—aryl—Q (VII) → pyrimidine—X—aryl—Q (VIII) → (ii) pyrimidine—X—aryl—YH (IX)]

Compounds of general formula IV:

[Formula IV: pyrimidine(A,B,D)—X—aryl(E,V)—Y—C(R¹)(R²)—W]

wherein A, B, D, E, V, W, X, Y, $R^1$ and $R^2$ are as hereinbefore defined may be prepared by:

(c) the condensation of the appropriate 5-hydroxy- or 5-mercapto- pyrimidine of general formula XI with a substituted benzene of general formula XII, wherein the substituent L is a good leaving group (for example, alkylsulfonyl, chlorine, bromine or iodine) and is activated with respect to displacement (for example, by being in a position ortho- or para- to an electron withdrawing substituent), preferably in the presence of an alkaline material, according to SCHEME G

SCHEME G

[Scheme G: pyrimidine-XH (XI) + L—aryl—Y—C(R¹)(R²)—W (XII) → product IV]

(d) the following steps in sequence:
  (i) the condensation of the appropriate 5-hydroxy- or 5-mercapto-pyrimidine of formula XI with a substituted benzene of formula XIII, wherein the substituent L is a good leaving group (for example, alkylsulfonyl, chlorine, bromine or iodine) and is activated with respect to displacement (for example, by being in a position ortho- or para- to an electron withdrawing substituent), preferably in the presence of an alkaline material, to give a compound of formula XIV wherein Q is hydroxy, mercapto, $C_1$ to $C_6$ alkylthio or $C_1$ to $C_6$ alkoxy;

(ii) the dealkylation of the compound of formula XIV prepared in step (i) above wherein Q is $C_1$ to $C_6$ alkoxy or $C_1$ to $C_6$ alkylthio to give a product of formula XV; and (iii) the condensation of the product of formula XV obtained in step (i) or step (ii) above with a compound of formula X according to the process described for SCHEME D above for the condensation of a compound of formula IX with a compound of formula X (Steps (i) and (ii) are shown in SCHEME J).

SCHEME J

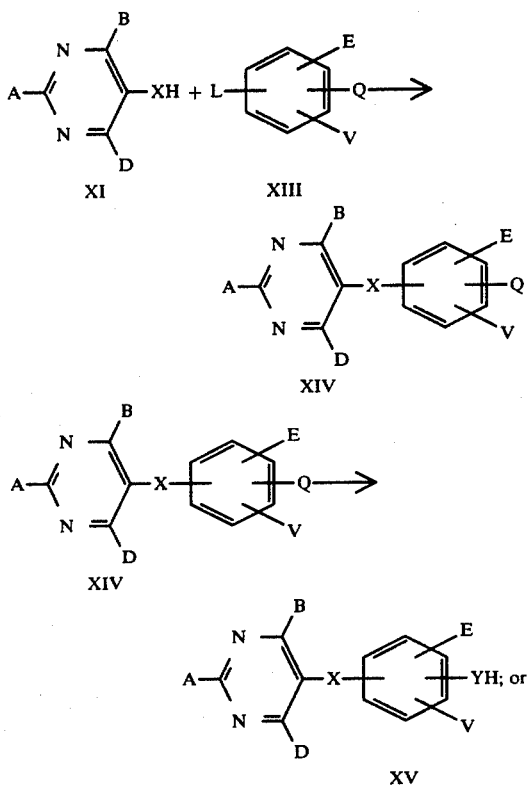

(e) the following steps in sequence:
 (i) the synthesis of the required 5-phenoxy- or 5-phenylthio- substituted pyrimidine of formula XIVa wherein Q is $C_1$ to $C_6$ alkoxy or $C_1$ to $C_6$ alkylthio;
 (ii) the dealkylation of the compound of formula XIVa to give a phenol or thiophenol of formula XVa; and
 (iii) the condensation of the product of formula XVa obtained in step (ii) above with a compound of formula X according to the process described for SCHEME D above for the condensation of a compound of formula IX with a compound of formula X (Steps (i) and (ii) are shown in SCHEME K).

SCHEME K

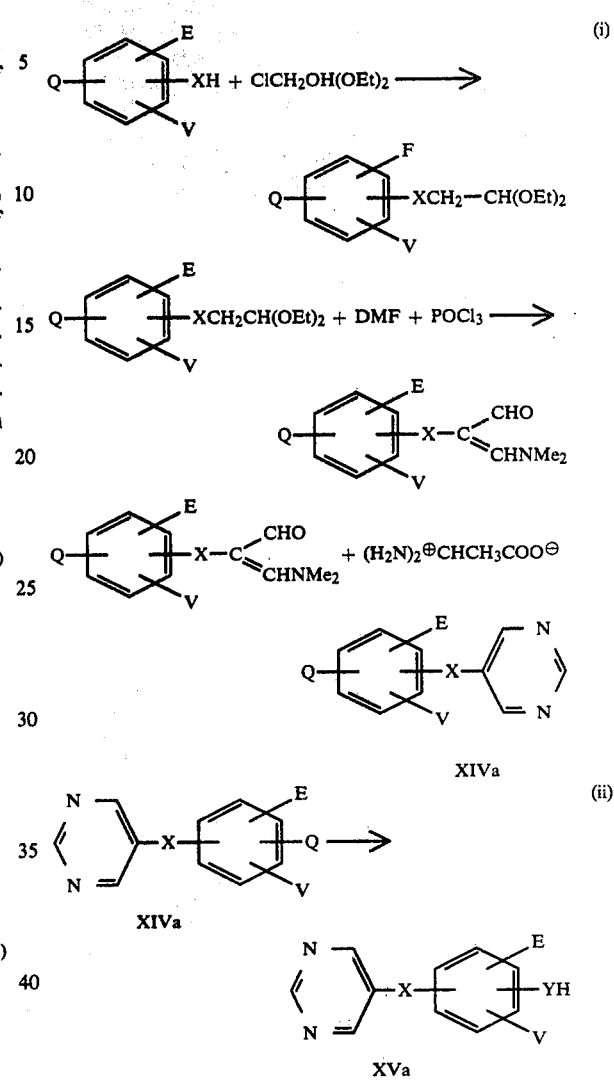

The condensation reactions illustrated in SCHEMES D, E, F, G and J and outlined above are preferably carried out in the presence of an alkaline material and preferably in the presence of a solvent. Suitable alkaline materials include, for example, the alkali and alkaline earth metal hydroxides and carbonates such as sodium hydroxide, potassium hydroxide, sodium carbonate and potassium carbonate. Suitable solvents include ketones such as, for example, acetone, methyl ethyl ketone and methyl isobutyl ketone, and dipolar aprotic solvents such as, for example, dimethylformamide, dimethylacetamide, dimethylsulfoxide, N-methylpyrrolidone, hexamethylphosphoramide and sulfolan.

The reaction conditions required to effect the condensation reactions illustrated in SCHEMES D, E, F, G and J and outlined above vary according to the nature of the reactants, the alkaline material and the solvents used. In general the reaction is facilitated by the application of heat and usually a reaction temperature in the range of 40° to 150° C. and reaction time of between 0.5 and 20 hours is satisfactory. However, higher or lower reaction temperatures and/or shorter or longer reaction times may be used if desired.

The dealkylation reactions illustrated in SCHEMES F, J and K and outlined in paragraphs (b)(ii), (d)(ii) and (e)(ii) above may be effected using a variety of reagents known in the art. For example, aryl-alkyl ethers may be cleaved using reagents such as pyridine hydrochloride, hydriodic acid, hydrobromic acid, sodium thioethoxide in dimethylformamide, acetyl p-toluene-sulphonate, sodium or potassium iodide in formic or acetic acid, lithium iodide in 2,4,6-collidine and borontribromide. Reaction times and reaction conditions vary widely depending on the dealkylation agent used and the ether to be cleaved. The reaction conditions generally employed when using the above "ether-cleavage" reagents are known to those skilled in the art and may be adapted without undue experimentation to effect the "ether-cleavage" reactions illustrated in SCHEMES F, J and K and outlined in paragraphs (b)(ii), (d)(ii) and (e)(ii) above.

The compounds of the invention are active as herbicides and therefore, in a further aspect the invention provides a process for severely damaging or killing unwanted plants which provess comprises applying to the plants, or to the growth medium of the plants, an effective amount of a compound of formula I as hereinbefore defined.

The compounds of the invention possess herbicidal activity against a variety of plants, both monocotyledonous and diocotyledonous. However, the compounds of the invention show selectivity in that certain crops, including cereal crops and in particular dicotyledonous crops, are relatively unaffected by rates of application of the compounds of the invention which are severely damaging or lethal to other plant species.

Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds are effective both when applied directly to the plants (post-emergence application) and when applied to the soil before the emergence of the plants (pre-emergence application. However, the compounds are, in general, more effective when applied to the plants post-emergence.

The rate of application of the compound will depend on various factors, such as the identity of the weeds and or crops being treated and the particular compound chosen for use. However, in general a rate of from 0.01 to 20 kilograms per hectare and preferably a rate from 0.1 to 2 kilograms per hectare will be suitable. The skilled worker in the art will readily be able to ascertain suitable application rates by standardised routine methods without undue experimentation.

The compounds 1, 14, 15, 16, 28, 67, 73, 74 and 75 of Table 1 have shown particularly good selectivity for the killing of weeds in dicotyledonous crops such as sunflower, cotton, soyabean, sugar beet and peanuts.

The compounds of the invention may be used on their own to inhibit the growth of, severely damage, or kill plants but are preferably used in the form of a composition comprising a compound of the invention in admixture with a carrier comprising a solid or liquid diluent. Therefore, in another aspect the invention provides plant growth inhibiting, plant damaging, or plant killing compositions comprising a compound of general formula I as hereinbefore defined and an inert carrier therefor.

Compositions according to the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (e.g. cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl- and triisopropyl-naphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octylcresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. These concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited the formulation selected for use and whether the compound is to be applied for foliage or root uptake. As a general guide, however, an application rate of from 0.01 to 20 kilograms per hectare is suitable while from 0.1 to 2 kilograms per hectate may be preferred.

It is to be understood that the compositions of this invention may comprise, in addition to one or more compounds of the invention, one or more compounds not of this invention which have biological activity.

The invention is now illustrated by, but by no means limited to, the following examples.

EXAMPLE 1

Preparation of Ethyl 2-[4-(5-bromo-2-pyrimidyloxy)phenoxy]propionate (1)

(a) 5-Bromo-2-chloropyrimidine (3.0 g), p-methoxyphenol (2.5 g), methyl ethyl ketone, (50 ml - dried over anhydrous potassium carbonate) and anhydrous potassium carbonate (2.5 g) were heated under reflux with stirring for 6 hours. The solvent was evaporated under reduced pressure, the residue treated with water and the precipitated compound collected by filtration. The product was treated with 5% sodium hydroxide aqueous solution and the mixture stirred for approximately 30 minutes. The solid was collected by filtration, washed with water and recrystallised from methanol/water to give 5-bromo-2-(4-methoxyphenoxy)-pyrimidine (3.4 g), m.p. 92° C.

(b) 5-Bromo-2-(4-methoxyphenoxy)pyrimidine (2.4 g) was dissolved in methylene chloride (50 ml) and the solution cooled to a temperature of −70° C. Boron tribromide (12.7 g) was added dropwise to the stirred solution, the temperature of the solution being maintained at −65° to −75° C. On completion of the addition the reaction mixture was stirred for a further one hour at a temperature of −65° to −75° C. and then the temperature of the reaction mixture was allowed to rise slowly to room temperature. The reaction mixture was added cautiously, in small portions, to water and the methylene chloride removed by heating the mixture on a water bath. The aqueous suspension was cooled to a temperature of 20° C., the solid was collected by filtration, washed with water and recrystallised from methanol/water to give 4-(5-bromo-2-pyrimidyloxy)phenol (2.1 g), m.p. 178° C.

(c) 4-(5-Bromo-2-pyrimidyloxy)phenol (1.45 g), ethyl 2-bromopropionate (1.1 g), methyl ethyl ketone (20 ml -dried over anhydrous potassium carbonate) and anhydrous potassium carbonate (1.0 g) were heated under reflux with stirring for 8 hours. The solvent was evaporated under reduced pressure and the residue treated with water. The mixture was extracted with methylene chloride, the methylene chloride extract dried over anhydrous sodium sulphate and the methylene chloride removed by evaporation under reduced pressure. The residue was purified by column chromatography over silica gel using chloroform as eluent to give a liquid (0.9 g) which was identified by proton magnetic resonance spectroscopy and mass spectrometry as the expected compound ethyl 2-[4-(5-bromo-2-pyrimidyloxy)phenoxy]propionate.

EXAMPLE 2

The compounds Nos. 3, 11, 12, 13, 14, 24, 25, 26, 27, 28, 29 and 32 of Table 1 and compounds no 76, 78 and 79 of Table 2 were prepared from the appropriate 2-chloropyrimidine, p-methoxyphenol and the appropriate 2-bromo-alkanoic acid alkyl ester according to the process described in Example 1 for the preparation of compound no. 1. The compounds were identified by proton magnetic resonance spectroscopy or mass spectrometry and the details are recorded in Example 21 Table 6 where appropriate.

EXAMPLE 3

Preparation of Ethyl 2-[4-(5-chloro-2-pyrimidylthio)-phenoxy] propionate (42)

(a) 5-Chloro-2-methylthio-4-pyrimidine carboxylic acid (30 g) was heated at 180°–200° C. until all the solid had melted and the evolution of carbon dioxide had ceased (5 min). The residue was allowed to cool and then washed with several portions of chloroform. The chloroform washings were filtered to remove dark insoluble material and the filtrate was concentrated to give 5-chloro-2-methylthiopyrimidine as a pale brown crystalline solid (21 g, 89%), m.p. 55° C.

(b) A solution of 5-chloro-2-methylthiopyrimidine (19 g) in acetic acid (45 ml) was treated with 30% hydrogen peroxide (45 ml) at 20° C. Initially a suspension was formed which cleared to a colourless solution after 24 hr, and then the 5-chloro-2-methylsulphonylpyrimidine slowly precipitated as large colourless crystals (15 g, 67%), m.p. 124° C., over a period of 5 days.

(c) Potassium carbonate (5.8 g) was added to a solution of 5-chloro-2-methylsulphonylpyrimidine (6.7 g) and 4-methoxythiophenol (5.0 g) in methyl ethyl ketone (50 ml) and the mixture was stirred and boiled under reflux for 3 hours. The solvent was evaporated under reduced pressure and the residue partitioned between chloroform and 5% sodium hydroxide aqueous solution. The chloroform extracts were dried (Mg SO$_4$) and evaporated under reduced pressure to give 5-chloro-2-(4-methoxyphenylthio)pyrimidine (8.5 g) as a colourless solid, m.p. 75° C.

(d) 5-Chloro-2-(4-methoxyphenylthio)pyrimidine (7.5 g) was dissolved in methylene chloride (60 ml) and the solution was cooled to −78° C. Boron tribromide (18 g) was added dropwise to the stirred solution, the temperature of the solution being maintained at −65° to −75° C. On completion of the addition the reaction mixture was stirred for a further one hour at −78° C. and then the temperature of the reaction mixture was allowed to rise slowly to 20° C. The reaction was quenched with water (50 ml), the resultant suspension cooled and filtered to give 4-(5-chloro-2-pyrimidylthio)phenol (5 g) as an almost colourless solid.

(e) 4-(5-chloro-2-pyrimidylthio)phenol (2.36 g), ethyl 2-bromopropionate (1.81 g), methyl ethyl ketone (20 ml) and anhydrous potassium carbonate (1.55 g) were heated under reflux with stirring for 16 hr. The solvent was removed under reduced pressure and the residue partitioned between chloroform and water. The chloroform layer was dried (MgSO₄) and the chloroform removed to give a liquid (4.0 g) which was chromatographed on silica gel (30 g) with chloroform elution to give a nearly colourless liquid which was identified by p.m.r. as ethyl 2-[4-(5-chloro-2-pyrimidylthio)phenoxy] propionate.

EXAMPLE 4

The compounds no 33 and 48 of Table 1 and 82 and 83 of Table 3 were prepared from the appropriate 2-(methylsulfonyl)-pyrimidine, the appropriate methoxy phenol and the appropriate 2-bromoalkanoic acid ester according to the process described in Example 3 for the preparation of compound no 42. The compounds were identified by proton magnetic resonance (p.m.r.) spectroscopy or mass spectrometry and the details are recorded in Example 21 Table 6.

EXAMPLE 5

The preparation of Ethyl 2-[4-(5-iodopyrimidyl-2-oxy)phenoxy] propionate (16)

(a) Methyl 2-bromopropionate (1 mole), p-methoxyphenol (1.15 mole) and anhydrous potassium carbonate (1.15 mole) were added to methyl ethyl ketone (c. 600 ml previously dried over anhydrous potassium carbonate) and the mixture was heated under reflux until no ethyl 2-bromopropionate could be detected by thin layer chromatography (c. 7 hr).

The solvent was removed by distillation under reduced pressure, water (c. 200 ml) was added and the product was extracted into methylene chloride. The extracts were dried (Na₂SO₄) and the solvent removed by distillation under reduced pressure to give an orange oil (93%) which was characterised by its p.m.r. spectrum as methyl 2-(4-methoxyphenoxy)propionate.

(b) Methyl 2-(4-methoxyphenoxy)propionate (33 g) hydrobromic acid (165 g of 48%) and glacial acetic acid (165 g) were mixed and heated under reflux until no ester could be detected by thin layer chromatography (c. 3 hr). The volume of the mixture was reduced to one third by distillation under reduced pressure and the mixture was poured onto ice (c. 300–400 g) and diluted to 600 ml with water and cooled with stirring to a temperature of c. 10° C. After stirring for 30 minutes the product was collected by filtration to give 13.3 g of a greyish powder, m.p. 145° C. The filtrate was evaporated to dryness, the residue was washed with hot methylene chloride and recrystallised from water to give a further 9.4 g of 2-(4-hydroxyphenoxy)propionic acid. Total yield 71%.

(c) 2-(4-hydroxyphenoxy)propionic acid (9.0 g), ethanol (15 ml) and concentrated sulfuric acid (0.5 ml) were added to ethylene dichloride (40 ml) and the mixture was heated under reflux overnight. The reaction mixture was cooled to room temperature and the ethylene dichloride layer was separated and washed twice with water and twice with aqueous 2% NaHCO₃. The organic fraction was dried over sodium sulfate and the solvent was removed by distillation under reduced pressure to give the product, ethyl 2-(4-hydroxyphenoxy)-propionate.

(d) A suspension of 2-amino-5-iodopyrimidine (40 g) in concentrated hydrochloric acid (150 ml) was treated dropwise at a temperature of 25° to 30° C. with a solution of sodium nitrate (40 g) in water (70 ml). The reaction mixture was stirred at a temperature of 25° to 30° C. for a further 2 hr and then neutralised by the addition of aqueous 20% sodium hydroxide, the temperature of the reaction mixture being maintained at 10° to 20° C. during the neutralisation by external cooling. The neutralised reaction mixture was filtered to remove solids and the solids were washed several times with chloroform. The filtrate was extracted with chloroform and the combined chloroform washings and extracts were dried and the chloroform was removed by distillation under reduced pressure to give crude 2-chloro-5-iodopyrimidine as a pale brown solid (12 g, 28%) with m.p. 125° C. (Reference m.p. 129°–130° C. J. Chem. Soc. (C), 1971, 1889).

(e) A mixture of 2-chloro-5-iodopyrimidine (1.5 g), ethyl 2-(4-hydroxyphenoxy)propionate (1.3 g), potassium carbonate (1.0 g) and methyl ethyl ketone (25 ml) was heated under reflux for a period of 18 hr.

The solvent was removed by distillation under reduced pressure and the residue was partitioned between water and chloroform. The chloroform layer was dried and the chloroform was removed by distillation under reduced pressure to give a dark oil (2.7 g). The product was chromatographed on silica gel (80 g), eluent chloroform, to give a colourless oil which was identified by its p.m.r. spectrum as ethyl 2-[4-(5-iodopyrimidyl-2-oxy)phenoxy]propionate.

EXAMPLE 6

The compounds no 17, 18, 20, 21 and 22 of Table 1 were prepared from the appropriate 2-chloropyrimidine and ethyl 2-(4-hydroxyphenoxy)propionate according to the process described in Example 5(e) for the preparation of compound no 16.

The compounds no 15, 37, 49 and 50 of Table 1 were prepared from the appropriate 2-chloropyrimidine and methyl 2-(4-hydroxyphenoxy)propionate essentially according to the process described in Example 5(e) for the preparation of compound no 16.

The compounds no 86 and 87 of Table 4 were prepared from the appropriate 4-chloropyrimidine and ethyl 2-(4-hydroxyphenoxy)-propionate essentially according to the process described in Example 5(e) for the preparation of compound no 16.

The compounds no 88, 89, 90 and 92 of Table 4 were prepared from the appropriate 4-chloropyrimidine and methyl 2-(4-hydroxyphenoxy)propionate essentialy according to the process described in Example 5(e) for the preparation of compound No. 16.

The compounds were identified by p.m.r. spectroscopy or mass spectrometry and the details are recorded in Example 21 Table 6.

EXAMPLE 7

Preparation of Methyl 2-[2-(5-Chloro-2-pyrimidyloxy)-4-chlorophenoxy] propionate (84)

Potassium carbonate (anhydrous, 1.52 g), 5-chloro-2-methylsulphonylpyrimidine (1.93 g), 2-(4-chloro-2-hydroxyphenoxy) propionic acid methyl ester (2.31 g) and methyl ethyl ketone (20 ml) were heated and stirred for 4 hours. The mixture was diluted with water and extracted with chloroform. The chloroform extracts were dried (MgSO$_4$) and the solvent removed to give a pale brown oil which was chromatographed on silica gel (40 g) with chloroform elution. The pure methyl 2-[2-(5-chloro-2-pyrimidyloxy)-4-chlorophenoxy] propionate was obtained as a colourless oil, and characterized by its p.m.r. spectrum.

EXAMPLE 8

The compounds no 23, 34, 39, 40, 46, 47, 61 and 94 of Table 1 were prepared from the appropriate 2-(methylsulfonyl)-pyrimidine and the appropriate methyl 2-(4-hydroxyphenoxy)-propionate essentially according to the process described in Example 7 for the preparation of compound no 84.

Compound no 52 of Table 1 was prepared from 5-ethoxy-2-(methylsulfonyl)pyrimidine and 2-(4-hydroxyphenoxy)propionic acid essentially according to the process described in Example 7 for the preparation of compound no 84.

The compounds no 31 and 35 of Table 1 were prepared from the appropriate 2-(methylsulfonyl)pyrimidine and the appropriate ethyl 2-(4-hydroxyphenoxy)-propionate essentially as described in Example 7 for the preparation of compound no 84.

The compounds no 80, 81 and 85 of Table 3 were prepared from the appropriate 2-(methylsulfonyl)-pyrimidine and the appropriate methyl 2-(2-hydroxyphenoxy)propionate according to the process described in Example 7 for the preparation of compound no 84.

The compounds were characterised by p.m.r. spectroscopy or mass spectrometry and the detals are recorded in Example 21 Table 6.

EXAMPLE 9

Preparation of 2-[4-(5-Bromopyrimidyl-2-oxy)phenoxy] propionic Acid (62)

Methyl 2-[4-(5-bromopyrimidyl-2-oxy)phenoxy] propionate (1.77 g) was dissolved in isopropanol (40 ml) and treated with stirring with a solution of sodium hydroxide (20 ml of solution containing 1 g per 100 ml) by dropwise additon at 20° C. The reaction mixture was stirred for 2½ hours before the solvents were evaporated under reduced pressure at 30° C. The residue was diluted with water (100 ml), acidified with 2 M hydrochloric acid until just acidic. The mixture was then extracted with ether (2×150 ml), the ether layer dried (MgSO$_4$) and concentrated to the crude 2-[4-(5-bromopyrimidyl-2-oxy)phenoxy]propionic acid (1.7 g).

EXAMPLE 10

The compounds no 30 and 51 were prepared from compounds 29 and 47 by hydrolysis according to the process described in Example 9 for the synthesis of compound no 62.

The compounds were characterised by p.m.r. spectroscopy and the details are recorded in Example 21 Table 6.

EXAMPLE 11

Preparation of Allyl 2-[4-(5-Bromopyrimidyl-2-oxy)phenoxy]propionate (36)

2-[4-(5-bromopyrimidyl-2-oxy)phenoxy]propionic acid (100 mg) was dissolved in thionyl chloride (2 ml) and stirred and heated at reflux for 2 hours. Thionyl chloride was removed under reduced pressure the residue azeotroped with toluene and this residue dissolved in toluene (5 ml) and treated with anhydrous potassium carbonate (100 mg) and allyl alcohol (100 mg). The reaction mixture was stirred at 20° C. for 1 hour, filtered, the residue washed with toluene and the toluene evaporated under reduced pressure to give allyl 2-[4-(5-bromopyrimidyl-2-oxy)-phenoxy]propionate as a colourless oil.

EXAMPLE 12

The compounds no 38, 43, 57, 58, 59, 60, 63, 64, 65, 66, 67, 68, 69, 70, 71 and 72, all esters of compound no 62, were prepared according to the process described in Example 11 for the synthesis of the ester, compound no 36.

The compounds no 41, 54, 55 and 56, all esters of compound no 62, were prepared by the reaction of 2-[4-(5-bromopyrimidyl-2-oxy)phenoxy]propionyl chloride with the appropriate amine essentially according to the process described in Example 11 for the synthesis of the ester, compound no 36.

The compounds were characterised by p.m.r. spectroscopy or mass spectrometry.

EXAMPLE 13

Preparation of Ethyl 2-[3-t-Butyl-4-(5-bromopyrimidyl-2-oxy)phenoxy]propionate (19)

(a) t-Butylhydroquinone (2.0 g), ethyl 2-bromopropionate (2.0 g), potassium carbonate (2.0 g, anhydrous) and methyl ethyl ketone (50 ml) were stirred and heated together under reflux for 8 hours. The reaction mixture was diluted with water (100 ml) and extracted with chloroform. The chloroform extracts were washed several times with water then dried (MgSO$_4$) and the chloroform removed to give a pale brown oil which was chromatographed on silica gel (40 g) with chloroform elution. Pure ethyl 2-(3-t-butyl-4-hydroxy) propionate was obtained as a colourless oil identified by p.m.r. spectroscopy.

(b) Potassium carbonate (0.7 g, anhydrous) was added to a solution of 5-bromo-2-chloropyrimidine (0.9 g) and ethyl 2-(3-t-butyl-4-hydroxyphenoxy)propionate (1.3 g) in methyl ethyl ketone (5 ml) and the mixture was stirred and heated under reflux for 24 hours. The reaction mixture was diluted with water and extracted with chloroform and the chloroform extracts were dried (MgSO$_4$) concentrated and chromatographed on silica gel (40 g) to give pure ethyl 2-[3-t-butyl-4-(5-bromopyrimidyl-2-oxy)phenoxy]propionate.

EXAMPLE 14

Preparation of Ethyl 2-[2-Nitro-4-(5-chloropyrimidyl-2-oxy)-phenoxy]propionate (45)

(a) A solution of 4-(5-chloro-2-pyrimidyloxy)phenol (1.4 g) in acetic acid (20 ml) was treated with fuming nitric acid (0.5 g) at 25° C. After 4 hours the mixture was poured into water and extracted with chloroform (2×100 ml). The chloroform extracts were dried (Mg2O4) and evaporated to a yellow solid which was chromatographed on silica gel (40 g). Elution with chloroform gave 4-(5-chloro-2-pyrimidyloxy)-2-nitrophenol (0.9 g) as pale yellow crystals.

(b) A mixture of 4-(5-chloro-2-pyrimidyloxy)-2-nitrophenol (0.9 g), ethyl 2-bromopropionate (0.7 g) and potassium carbonate (0.5 g) in methyl ethyl ketone (30 ml) was stirred and heated under reflux for 16 hours. The solvent was removed under reduced pressure and the residue was partitioned between chloroform and water. The chloroform extracts were dried (MgSO4) and evaporated to give a colourless solid which was recrystallized from ethanol to give ethyl 2-[2-nitro-4-(5-chloropyrimidyl-2-oxy)phenoxy]propionate as colourless needles (0.66 g) m.p. 82° C.

EXAMPLE 15

Compound no 77 of Table 2 was prepared by the nitration of 3-(5-chloro-2-pyrimidyloxy)phenol followed by the reaction of the 3-(5-chloro-2-pyrimidyloxy)-6-nitrophenol thus prepared with ethyl 2-bromopropionate essentially according to the process described in Example 14 for the preparation of compound no 45.

EXAMPLE 16

Preparation of Ethyl 2-[2-Trifluoromethyl-4-(5-chloropyrimidyl-2-oxy)-phenoxy]propionate (53)

(a) Trifluoromethylhydroquinone (2.05 g), 5-chloro-2-methylsulphonylpyrimidine (2.15 g) and potassium carbonate (1.75 g, anhydrous) were stirred and heated together under reflux in methyl ethyl ketone (30 ml) for 3 hours. The reaction mixture was partitioned between water and chloroform, the chloroform layer was dried (MgSO4) and evaporated to a semi crystalline solid which was chromatographed on silica gel (100 g). Chloroform elution gave initially, 1,4-bis-(5-chloropyrimidyl-2-oxy)-2-trifluoromethylbenzene and then 4-(5-chloro-pyrimidyl-2-oxy)-2-trifluoromethylphenol (1.2 g) as the major product.

(b) 4-(5-Chloropyrimidyl-2-oxy)-2-trifluoromethylphenol (1.2 g), ethyl-2-bromopropionate (1.1 g), methyl ethyl ketone (20 ml) and anhydrous potassium carbonate (0.8 g) were heated under reflux with stirring for 16 hours. The solvent was removed under reduced pressure and the residue was partitioned between chloroform and water. The chloroform layer was dried and the chloroform evaporated to give ethyl 2-[2-trifluoromethyl-4-(5-chloropyrimidyl-2-oxy)phenoxy]-propionate as a colourless oil (1.2 g).

EXAMPLE 17

Preparation of Methyl 2-[4-(5-bromo-2-dimethylaminopyrimidyl-4-oxy)-phenoxy]propionate (91)

Aqueous dimethylamine (1.5 ml, 25%) was added to methyl 2-[4-(5-bromo-2-chloropyrimidyl-4-oxy)-phenoxy]propionate (1.2 g) in methanol (5 ml) with stirring and the suspension was stirred at 20° C. for 48 hours. The suspension was filtered and washed with water. The residue was dissolved in acetone, filtered to remove insoluble material and the acetone removed to give a solid which was washed with methanol and collected by filtration. Proton magnetic resonance and mass spectra identified the solid (0.7 g), m.p. 108° C. as methyl 2-[4-(5-bromo-2-dimethylaminopyrimidyl-4-oxy)phenoxy]propionate.

EXAMPLE 18

Preparation of Methyl 2-[2-(5-Trifluoromethylpyrimidyl-2-oxy)phenoxy]propionate (73)

(a) 2-Amino-5-trifluoromethylpyrimidine. 2-Amino-5-carboxypyrimidine (16.5 g), SF4 (36 g) and HF (100 g) were heated in an autoclave at 120° C. for 8 hours with stirring. The product was washed from the autoclave with water and poured onto ice (about 1.5 liters) and basified with 10 N sodium hydroxide solution. The mixture was filtered and the filter cake dried, powdered, and extracted with ether (2×400 ml). The ether extracts gave 2-amino-5-trifluoromethyl pyrimidine (9 g).

(b) 2-Bromo-5-trifluoromethylpyrimidine. The above 2-amino-5-trifluoromethyl pyrimidine (3.6 g) dispersed in aqueous hydrobromic acid (11 ml of 48–50% solution) was treated dropwise with bromine (3.4 g) over a period of about 10 minutes, with stirring, and kept at 0° C. The thick slurry so obtained was kept at 0° C. for another 15 minutes. A solution of sodium nitrate (3.88 g) in water (6 ml) was then added dropwise at 0° C. over a period of 30 minutes. When addition was complete the mixture was stirred for 30 minutes with ice bath cooling and then for 15 minutes at room temperature. The mixture was then poured on to ice (about 150 ml) and made just basic with 2 M sodium hydroxide the mixture was extracted with ether (200 ml) and the ether extracts washed with water, dried (MgSO4) and evaporated to give an oil which solidified on cooling. The solid was extracted with petroleum ether (B.P. 30°–40° C.) leaving a gum behind. The petroleum extracts were evaporated to give 2-bromo-5-trifluoromethyl pyrimidine.

(c) Methyl 2-[2-(5-trifluoromethylpyrimidyl-2-oxy)-phenoxy]propionate, compound No 73 was prepared from 2-bromo-5-trifluoromethylpyrimidine and methyl 2-(4-hydroxyphenoxy) propionate essentially according to the process described in Example 5e) for the preparation of compound No 16.

The compounds No 74 and 75 also were prepared from 2-bromo-5-trifluoromethylpyrimidine and the appropriate 2-(4-hydroxyphenoxy)propionic acid ester by essentially the same process.

EXAMPLE 19

Preparation of 2-Chloro-5-trifluoromethylpyrimidine (a) 2-Chloro-5-methylpyrimidine (5.0 g) was finely powdered and dissolved in dry carbon tetrachloride (250 ml). The solution was treated with dry hydrogen chloride gas to precipitate the hydrochloride salt. The reaction mixture was heated to reflux and illuminated with an internal ultra-violet lamp whilst chlorine was bubbled through the stirred suspension. After 4½ hours the solution was cooled and filtered and the filtrate concentrated under reduced pressure to give a semi-crystalline residue. The residue was dissolved in ether and filtered and the filtrate concentrated to a colourless oil which on standing gave crystals of 2-chloro-5-trichloromethylpyrimidine (8.9 g).

(b) Antimony trifluoride (18 g) was fused by heating with a bunsen burner to remove residual water. The melt was cooled and broken up. Antimony pentachloride (17 g) was added dropwise to the stirred solid at 75°–80° C. and stirring was continued for 0.25 hour after the addition was complete. 2-Chloro-5-trichloromethylpyrimidine (8.9 g) was warmed to give a liquid and added dropwise to the above suspension. The mixture was gradually heated to 155°–160° C. over 0.75 hours and then allowed to cool.

The reaction mixture was cautiously treated with water (100 ml), the solid was broken up and the suspension diluted to 300 ml with further water containing tartaric acid (100 g). The aqueous mixture was extracted with diethyl ether (2×150 ml) and the ether layer was washed with further tartaric acid solution (100 g in 200 ml water), then water (2×150 ml), saturated bicarbonate solution (200 ml) and finally water (2×150 ml).

The ether layer was dried ($MgSO_4$) and the solution distilled at atmospheric pressure. Ether was collected from 20° to 35° C. and then the 2-chloro-5-trifluoromethylpyrimidine distilled at 140°–144° C. as a colourless liquid which solidified slowly at room temperature. The purity and identity of the distillate was established by G.L.C., p.m.r. and a mass spectrum.

2-Chloro-5-trifluoromethylpyrimidine may be used in the preparation of (5-trifluoromethylpyrimidyl-2-oxy)-phenoxypropionates of formula I according to the process described in Example 18 c) above.

EXAMPLE 20

Preparation of Methyl 2-[4-(Pyrimidyl-5-oxy)phenoxy]-propionate (93)

(a) Potassium hydroxide pellets (22.4 g) and molten p-methoxyphenol (50 g) were heated with stirring to a temperature in the range from 90° to 100° C. until a clear solution was obtained. Chloroacetaldehyde diethylacetal (120 g) was added at such a rate to maintain the temperature in the range from 90° to 100° C. and after stirring for a further 15 minutes water was removed from the flask as an azeotrope with chloroacetaldehyde diethylacetal, the water and acetal were separated and the acetal was returned to the reaction mixture. Azeotropic distillation was continued until the temperature of the vapour reached 140°–150° C. and then the reaction mixture was heated under reflux for a further 6 hr. Water (200 ml) was added to the cooled mixture which was then extracted with chloroform (2×200 ml). The choroform extracts were washed with aqueous 2 N sodium hydroxide (100 ml) to remove unreacted phenols and the chloroform layer was dried over $Na_2SO_4$ and the solvent removed by distillation under reduced pressure. The crude product was distilled under reduced pressure to give, as a third fraction, p-methoxyphenoxyacetaldehyde diethyl acetal (45.6 g) of b.p. 180°–194° C. at 44 mm the product being characterised by p.m.r. spectroscopy.

(b) Dry dimethylformamide (20 ml) was added dropwise to a stirred solution of phosphorus oxychloride (18 ml) maintained at a remperature of 0° C. The reaction mixture was allowed to warm to room temperature and p-methoxyphenoxyacetaldehyde diethyl acetal (16 g) was added with stirring. The mixture was cautiously heated with stirring to a temperature of 90° C. and then maintained at that temperature for 6 hr. The mixture was then cooled and poured slowly onto crushed ice (c. 1 kg) and the pH of the solution adjusted to pH10 by the addition, with stirring, of solid potassium carbonate. A benzene (95%)/alcohol (5%) solution (500 ml) was added to the reaction mixture and the total mixture heated just below its boiling point for 2 hr. The mixture was cooled, the organic layer was separated and dried, and the solvent removed by distillation under reduced pressure to give a black oil. The product crystallised from ethanol, after treatment with charcoal, to give 2-(p-methoxyphenoxy)-3-(dimethylamino)-acrolein (6.4 g) which was characterised by p.m.r. spectroscopy.

(c) Sodium metal (4.1 g) was dissolved in absolute ethanol (90 ml) and formamidine acetate (18.4 g) and 2-(p-methoxyphenoxy)-3-(dimethylamino)acrolein (13.0 g) were added to the ethanolic solution of sodium ethoxide. The mixture was heated under reflux, with stirring, for 40 hr and then the solvent was removed, by distillation under reduced pressure. The residue was treated with water (200 ml) and chloroform (200 ml), the chloroform layer was separated and the chloroform removed by distillation under reduced pressure. The residue was purified by column chromatography over silica gel using chloroform as eluent to give 5-(p-methoxyphenoxy)pyrimidine as an oil (7.7 g) which was characterised by p.m.r. spectroscopy.

(d) 5-(p-Methoxyphenoxy)pyrimidine (7.7 g) was dissolved in dichloromethane and the solution, maintained at a temperature of −70° to −78° C., was treated by the dropwise addition of boron tribromide (7 ml). The stirred solution was allowed to warm to room temperature and after standing overnight the dichloromethane solution was washed with a cold saturated aqueous solution of sodium bicarbonate (100 ml). The dichloromethane solution was then dried, treated with charcoal and the solvent removed by distillation under reduced pressure. The residue was washed with diethyl ether to give 5-(p-hydroxyphenoxy)pyrimidine (0.4 g) m.p. 158° C. which was characterised by p.m.r. spectroscopy.

(e) A mixture of 5-(p-hydroxyphenoxy)pyrimidine (0.4 g), methyl 2-bromopropionate (0.43 g), anhydrous potassium carbonate (0.29 g) and methyl ethyl ketone (20 ml) was heated under reflux with stirring for 4 hr. The solvent was evaporated under reduced pressure, the residue was treated with water and the mixture was extracted with chloroform. The chloroform extracts were dried ($Na_2SO_4$) and the chloroform was removed by distillation under reduced pressure. The residue was purified by chromatography over silica gel using chloroform as eluent to give an oil (0.4 g) which was identified by p.m.r. spectroscopy and mass spectrometry as methyl 2-[4-(pyrimidyl-5-oxy)-phenoxy]propionate.

EXAMPLE 21

The majority of the compounds of the invention are oils and were characterised by and may be identified by p.m.r. spectroscopy. For convenience the p.m.r. spectroscopy data, mass spectrometric data, melting points and boiling points, where appropriate, are recorded in Table 6 below.

TABLE 6

Partial Proton Magnetic Resonance Data on the compounds of formula

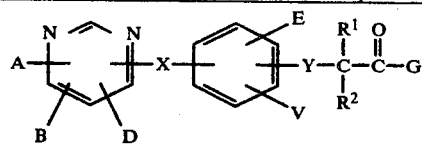

| Compound No. | Pyrimidyl Protons | Phenyl Protons | R² Protons | R¹ Protons | Group G Protons | m.p. or b.p. °C. |
|---|---|---|---|---|---|---|
| 11 | 8.5 (2H, d) 7.0 (1H, d) | 7.0(m) | 4.6(2H, s) | | 4.25 (2H, q) 1.25 (3H, t) | |
| 12 | 8.4(2H, d) 6.8(1H, d) | 6.8(m) | 4.5(1H, q) | 1.4(3H, d) | 4.0(2H, q) 1.0(3H, t) | |
| 1 | 8.55(2H, s) | 7.0(m) | 4.75(1H, q) | 1.6(3H, d) | 4.25(2H, q) 1.25(3H, t) | |
| 3 | 8.75(2H, s) | 7.3(m) | 4.8(2H, s) | | 4.4(2H, q) 1.4(3H, t) | |
| 13 | 8.5(2H, s) | 7.0(m) | 4.7(1H, q) | 1.5(3H, d) | 4.2(2H, q) 1.2(3H, s) | |
| 14 | 8.5(2H, s) | 7.0(m) | 4.8(1H, q) | 1.6(3H, d) | 3.8(3H, s) | |
| 15 | 8.6(2H, s) | 7.0(m) | 4.8(1H, q) | 1.6(3H, d) | 3.8(3H, s) | |
| 16 | 8.7(2H, s) | 7.0(m) | 4.7(1H, q) | 1.6(3H, d) | 4.2(2H, q) 1.2(3H, t) | |
| 17 | 6.9(1H, s) | 7.1(m) | 4.9(1H, q) | 1.7(3H, d) | 4.3(2H, q) 1.3(3H, t) 2.5(6H, s) | |
| 18 | — | 7.1(m) | 4.9(1H, q) | 1.7(3H, d) | 4.3(2H, q) 1.3(3H, t) 2.7(6H, s) | |
| 86 | 6.4(1H, s) | 7.0(m) | 4.8(1H, q) | 1.7(3H, d) | 4.3(2H, q) 1.3(3H, t) 2.6(3H, s) 2.4(3H, s) | |
| 20 | 8.5(1H, s) | 7.0(m) | 4.75(1H, q) | 1.6(3H, d) | 4.2(2H, q) 1.3(3H, t) 2.6(3H, s) | |
| 19 | 8.6(2H, s) | 6.5–7.1(m) | 4.7(1H, q) | 1.6(3H, d) | 4.2(3H, q) 1.3(12H, bs) | |
| 21 | 8.8(2H, s) | 7.1 (m) | 4.7(1H, q) | 1.7(3H, d) | 4.2(2H, q) 1.3(3H, t) 8.5(5H, s) | 91° |
| 22 | | | | | | 102° |
| 87 | 6.8(1H, d) 8.5(1H, d) | 7.1 (m) | 4.9(1H, q) | 1.7(3H, d) | 3.9(3H, s) | 90° |
| 88 | 8.6(1H, s) 6.9(1H, s) | 7.0 (m) | 4.8(1H, q) | 1.6(3H, d) | 3.8(3H, s) | 68° |
| 23 | 9.2(2H, s) | 7.1 (m) | 4.8(1H, q) | 1.7(3H, d) | 4.4(2H, q) 3.8(3H, s) 1.4(3H, t) | 81° |
| 24 | 8.6(2H, s) | 7.0 (m) | 1.5(6H, s) | | 4.2(2H, q) 1.2(3H, t) | |
| 25 | 8.6(2H, s) | 7.0 (m) | 4.5(1H, t) | 1.0–2.2 (5H, m) | 4.3(2H, q) | |
| 26 | 8.6(2H, s) | 7.0 (m) | 4.6(1H, t) | 0.9–2.2 (16H, m) | 4.3(2H, q) | |
| 27 | 8.5(2H, s) | 7.0 (m) | 1.6(6H,s) | | 4.2(2H, q) 1.2(3H, t) | |
| 28 | 8.6(2H, s) | 7.0 (m) | 4.8(1H, q) | 1.7(3H, d) | 4.2(2H, t) 0.8–1.8 (7H, m) | |
| 29 | 8.4(2H, s) | 7.0 (m) | 4.8(1H, q) | 1.6(3H, d) | 4.2(2H, q) 2.2(3H, s) 1.2(3H, t) | |
| 30 | 8.4(2H, s) | 7.0 (m) | 4.8(1H, q) | 1.6(3H, d) | 2.2(3H, s) | |
| 31 | 8.6(1H, s) | 7.0 (m) | 4.7(1H, q) | 1.6(3H, d) | 4.5(2H, q) 4.2(2H, q) 1.4(3H, t) 1.2(3H, t) | |
| 89 | *a* | | | | | |

TABLE 6-continued

Partial Proton Magnetic Resonance Data on the compounds of formula

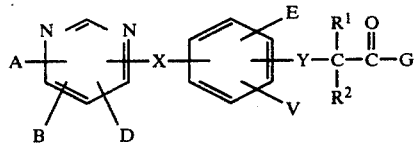

| No | B | D | R² | R¹ | Group G | b.p. |
|---|---|---|---|---|---|---|
| 90 | 8.7(1H, s) | 7.1 (m) | 4.8(1H, q) | 1.7(3H, d) | 3.8(3H, s) | 108° |
| 91 | | | | | | 108° |
| 32 | 8.3(1H, s) | 7.0 (m) | 4.8(1H, q) | 1.6(3H, d) | 4.0(3H, s) 3.7(3H, s) | |
| 35 | 8.5(2H, s) | 6.5–7.0 (3H, m) | 4.7(1H, q) | 1.6(3H, d) | 4.3(2H, q) 1.3(3H, t) | |
| 80 | 8.6(2H, s) | 6.8–7.2 (3H, m) | 4.7(1H, q) | 1.4(3H, d) | 3.7(3H, s) | |
| 36 | 8.5(2H, s) | 7.0 (m) | | 1.6(3H, d) | 4.5–5.5[b] (6H, m) | |
| 37 | 8.7(2H, s) | 7.0 (m) | 4.8(1H, q) | 1.6(3H, d) | 3.8(3H, s) | |
| 38 | 8.6(2H, s) | 7.0 (m) | | 1.6(3H, d) | 4.8–5.2[b] (3H, m) 2.5(1H, m) | |
| 39 | 8.8(2H, s) | 7.1 (m) | 4.8(1H, q) | 1.6(3H, d) | 7.5(4H, s) 3.8(3H, s) | 118° |
| 40 | 9.0(2H, s) | 7.1 (m) | 4.8(1H, q) | 1.6(3H, d) | 8.2(4H, d of d) 3.8(3H, s) | 170° |
| 77 | 8.6(2H, s) | 6.8–8.2 (3H, m) | 4.8(1H, q) | 1.6(3H, d) | 4.2(2H, q) 1.2(3H, t) | |
| 41 | 8.7(2H, s) | 7.0 (m) | 4.8(1H, q) | 1.6(3H, d) | 3.3(4H, m) 1.2(6H, m) | |
| 42 | 8.5(2H, s) | 7.3 (m) | 4.8(1H, q) | 1.6(3H, d) | 4.3(2H, q) 1.3(3H, t) | |
| 43 | 8.6(2H, s) | 7.0 (m) | 4.6(1H, q) | 1.5(9H, bs) | | |
| 81 | 8.5(2H, s) | 6.8–7.3 | 4.7(1H, q) | 1.3 (3H, d) | 3.7(3H, s) | |
| 45 | | | | | | 82° |
| 46 | 8.6(2H, s) | 7.3 (m) | 3.9(1H, q) | 1.5(3H, d) | 3.7(3H, s) | |
| 82 | 8.5(2H, s) | 6.8–7.3 (3H, m) | 4.7(1H, q) | 1.4(3H, d) | 3.7(3H, s) | |
| 49 | 8.5(2H, s) | 7.0(m) | 4.8(1H, q) | 1.6(3H, d) | 3.7(3H, s) | |
| 50 | 8.7(2H, s) | 6.8–7.3 (3H, m) | 4.7(1H, q) | 1.6(3H, d) | 3.8(3H, s) | |
| 84 | 8.5(2H, s) | 6.7–7.3 (3H, 4.2(2H, | 4.7(1H, q) | 1.4(3H, d) | 3.7(3H, s) | |
| 53 | 8.5(2H, s) | 6.8–7.5 (3H, m) | 4.8(1H, q) | 1.7(3H, d) | 4.(2H, q) | |
| 52 | 8.3(2H, s) | 7.0 (m) | 4.8(1H, q) | 1.6(3H, d) | 8.5(1H, bs) 4.1(2H, q) [c] 1.3(3H, t) | |
| 85 | 8.9(2H, s) | 6.9–7.3 (3H, m) | 4.8(1H, q) | 1.4(3H, d) | 8.1(4H, d of d) 3.7(3H, s) | |
| 54 | 8.6(2H, s) | 6.8–7.3[d] (7H, m) | 4.8(1H, q) | 1.6(3H, d) | 4.8(2H, m) | |
| 55 | [e] | | | | | |
| 56 | [f] | | | | | |
| 57 | 8.6 (2H, s) | 7.1 (m) | 5.1(1H, q) | 1.8(3H, d) | 7.8(4H, d of d) | |
| 58 | 8.6(2H, s) | 7.0 (m) | 4.8(1H, q) | 1.6(3H, d) | 7.4(5H, s) 5.2(2H, s) | |
| 59 | 8.6(2H, s) | 7.0 (m) | 4.5–5.3[g] (6H, m) | 1.6(3H, d) | | |
| 60 | 8.6(2H, s) | 7.0 (m) | 4.8(1H, q) | 1.6(3H, d) | 7.3(5H, s) 4.2(2H, s) | |
| 61 | 8.5(1H, d) | 6.7–7.2[h] (5H, m) | 4.8(1H, q) | 1.6(3H, d) | 3.8(3H, s) | 122° |
| 94 | 8.4(2H, s) | 6.7–7.4[j] (8H, m) | 4.8(1H, q) | 1.6(3H, d) | 3.8(3H, s) | |
| 73 | 8.9(2H, s) | 7.0(4H,m) | 4.8(1H, q) | 1.7(3H, d) | 3.8(3H, s) | |
| 93 | 8.9(1H, s) 8.4(2H, s) | 6.9 (m) | 4.8(1H, q) | 1.6(3H, d) | 3.8(3H, s) | |

| | CHEMICAL SHIFT IN δppm | | | | | |
|---|---|---|---|---|---|---|
| Compound No | Pyrimidyl Protons | Phenyl Protons | R² Protons | R¹ Protons | Group G Protons | b.p. |
| 92 | | | | | | 180–200/ 0.15 mm |
| 78 | | | | | | 170– |

TABLE 6-continued

Partial Proton Magnetic Resonance Data on the compounds of formula

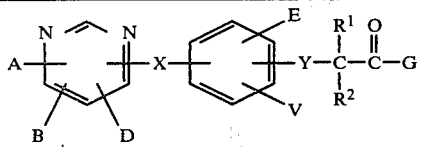

| | | |
|---|---|---|
| 79 | | 200/<br>0.4 mm<br>200–<br>215/<br>0.25 mm |

[a] Mass spectra m/e: 288 (M$^+$), 215, 187
[b] Includes R$^2$ proton
[c] Ethoxy group protons on pyrimidyl ring
[d] Includes Thienyl protons
[e] Mass spectra m/e: 407 (M$^+$)
[f] Mass spectra m/e: 415 (M$^+$)
[g] Includes allyl protons
[h] Includes one pyrimidyl proton
[j] Includes 3—Cl—C$_6$H$_4$—O— group protons

EXAMPLE 22

Concentrated formulations of the compounds of the invention were prepared by adding 4 parts by weight of the active ingredient to 96 parts by weight of "Lubrol" E (a registered Trade Mark for a condensation product of alkylphenol with ethylene oxide) and ball-milling the mixture to produce a stable suspension. The concentrated suspension was then diluted with water to give an aqueous composition suitable for use in the evaluation of the pre-emergence and post-emergence herbicidal activity of the compound.

The pre-emergent herbicidal activity of the compositions prepared according to the process above was assessed by the following procedure.

The seeds of the test species were sprinkled onto the surface of soil in each of five seed boxes and covered with a thin layer of sand. Each of four boxes was then sprayed with a quantity of a composition of the invention and the remaining box was sprayed with an equivalent volume of water for comparison purposes. The boxes were then lightly watered with an overhead spray and placed in a glasshouse to encourage germination of the seeds. Three weeks later the boxes were removed from the glasshouse and the effect of the treatment visually assessed. The results are presented in Table 7.

The post-emergent herbicidal activity of the compositions prepared according to the process above was assessed by the following procedure.

The seeds of the test species were sprinkled onto the surface of soil in seed boxes and covered with a thin layer of sand. The boxes were lightly watered with an overhead spray and placed in a glasshouse for one week to permit germination of the seeds and plant growth to a height of 4 to 5 inches. The boxes were then removed from the glasshouse and sprayed with a composition of the invention. For comparison purposes at least one box containing one week old seedlings was sprayed lightly with water only. After spraying the boxes were returned to the glasshouse for a further 3 weeks and the effect of the treatment was visually assessed. The results are presented in Table 7.

In Table 7 the damage to plants is rated on a scale of 0 to 3 where 0 represents from 0 to 25% damage and 3 represents 90 to 100% kill. A dash (-) means that no experiment was carried out.

TABLE 7

| Compound No | Pre- or Post-Emergence Application | Rate of Application kg/ha | TEST PLANT | | | | | | | |
|---|---|---|---|---|---|---|---|---|---|---|
| | | | Wh | Ot | Rg | Jm | P | IP | Ms | Sf |
| 1 | PRE | 5.0 | 3 | 3 | 3 | 3 | 0 | 0 | 0 | 1 |
| 1 | PRE | 1.0 | 2 | 2 | 3 | 3 | 0 | 2 | 0 | 2 |
| 1 | PRE | 0.5 | 1 | 2.5 | 3 | 3 | 0 | 1 | 0 | 1 |
| 1 | POST | 5.0 | 3 | 3 | 3 | 3 | 0 | 0 | 0 | 0 |
| 1 | POST | 1.0 | 2 | 3 | 3 | 3 | 0 | 0 | 2 | 0 |
| 1 | POST | 0.5 | 3 | 3 | 3 | 3 | 0 | 0 | 1 | — |
| 13 | PRE | 5.0 | 2 | 3 | 3 | 3 | 0 | 2.5 | 0 | 1 |
| 13 | PRE | 1.0 | 1 | 2 | 3 | 3 | 0 | 2 | 0 | 2 |
| 13 | PRE | 0.5 | 1 | 0 | 2 | 3 | 0 | 1 | 0 | 1 |
| 13 | POST | 5.0 | 2.5 | 3 | 3 | 3 | 0 | 0 | 0 | — |
| 13 | POST | 1.0 | 2 | 3 | 3 | 3 | 0 | 0 | 0 | — |
| 13 | POST | 0.5 | 2 | 2.5 | 3 | 3 | 0 | 0 | 0 | — |
| 14 | PRE | 5.0 | 2.5 | 3 | 3 | 3 | 0 | 1 | 1 | — |
| 14 | PRE | 1.0 | 2.5 | 2 | 3 | 3 | 0 | 1 | 0 | 2 |
| 14 | POST | 5.0 | 3 | 3 | 3 | 3 | 0 | 0 | 0 | 0 |
| 14 | POST | 1.0 | 2 | 3 | 3 | 3 | 0 | 0 | 0 | 0 |
| 14 | POST | 0.5 | 2 | 2 | 3 | 3 | 0 | 0 | 0 | 0 |
| 15 | PRE | 5.0 | 3 | 3 | 3 | 3 | 0 | 1 | 0 | 0 |
| 15 | PRE | 1.0 | 2.5 | 3 | 3 | 3 | 0 | 0 | 0 | 0 |
| 15 | POST | 5.0 | 3 | 3 | 3 | 3 | 0 | 0 | 0 | 0 |
| 15 | POST | 1.0 | — | 3 | 3 | 3 | 0 | 0 | 0 | 0 |
| 16 | PRE | 5.0 | 3 | 3 | 3 | 3 | 0 | — | 0 | — |
| 16 | PRE | 1.0 | 3 | 3 | 3 | 3 | 0 | — | 0 | — |
| 16 | PRE | 0.5 | 2 | 0 | 3 | 3 | 0 | 0 | 0 | 0 |
| 16 | PRE | 0.1 | 0.5 | 0 | 1.5 | 3 | 0 | 0 | 0 | 0 |
| 16 | POST | 5.0 | 3 | 3 | 3 | 3 | 0 | 1 | 0 | — |
| 16 | POST | 1.0 | 3 | 3 | 3 | 3 | 0 | 0 | 0 | 0 |
| 16 | POST | 0.5 | 2.5 | 3 | 3 | 3 | — | — | — | — |
| 16 | POST | 0.1 | 2 | 3 | 3 | 3 | — | — | — | — |
| 17 | POST | 5.0 | 0 | 0 | 0 | 0 | 2 | 0 | 1 | 0 |
| 18 | POST | 5.0 | 0 | 0 | 0 | 1 | 0 | 0 | 0 | 0 |
| 20 | PRE | 5.0 | 2 | 0 | 3 | 3 | 0 | 0 | 0 | 0 |
| 20 | PRE | 1.0 | 0 | 0 | 0 | 0 | 0 | 0 | 0 | 0 |
| 20 | POST | 5.0 | 2 | 2.5 | 2 | 3 | 0 | 0 | 0 | 0 |
| 20 | POST | 1.0 | 0 | 0 | 1 | 2 | 0 | 0 | 0 | 0 |
| 21 | PRE | 5.0 | 3 | 0 | 3 | 3 | 0 | 0 | 0 | 0 |
| 21 | PRE | 1.0 | 1 | 0 | 2 | 2 | 0 | 0 | 0 | 0 |
| 21 | POST | 5.0 | 3 | 2 | 2 | 3 | 0 | 0 | 0 | 0 |
| 21 | POST | 1.0 | 0 | 0 | 1 | 3 | 0 | 0 | 0 | 0 |
| 24 | POST | 5.0 | 1 | 0 | 0 | 3 | 0 | 0 | 0 | 0 |
| 25 | PRE | 5.0 | 2 | 1 | 3 | 3 | 0 | 0 | 2 | 0 |
| 25 | PRE | 1.0 | 0 | 0 | 0 | 2 | 0 | 0 | 0 | 0 |
| 25 | POST | 5.0 | 3 | 3 | 3 | 3 | 0 | 0 | 0 | 0 |
| 25 | POST | 1.0 | 2 | 2 | 2 | 3 | 0 | 0 | 0 | 0 |
| 27 | POST | 5.0 | 0 | 0 | 0 | 2 | 0 | 0 | 0 | 0 |
| 28 | PRE | 5.0 | 3 | 3 | 3 | 3 | 0 | 0 | 0 | 0 |
| 28 | PRE | 1.0 | 3 | 2 | 3 | 3 | 0 | 0 | 0 | 0 |
| 28 | POST | 5.0 | 3 | 3 | 3 | 3 | 0 | 0 | 3 | 0 |
| 28 | POST | 1.0 | 3 | 3 | 3 | 3 | 0 | 0 | 1 | 0 |
| 31 | PRE | 5.0 | 1 | 0 | 0 | 3 | 0 | 0 | 0 | 0 |
| 31 | POST | 5.0 | 2 | 0 | 0 | 3 | 0 | 0 | 0 | 0 |

TABLE 7-continued

| Compound No | Pre- or Post-Emergence Application | Rate of Application kg/ha | Wh | Ot | Rg | Jm | P | IP | Ms | Sf |
|---|---|---|---|---|---|---|---|---|---|---|
| 32 | PRE | 5.0 | 1 | 0 | 0 | 3 | 0 | 0 | 0 | 0 |
| 32 | POST | 5.0 | 2 | 0 | 0 | 3 | 0 | 0 | 0 | 0 |
| 33 | PRE | 1.0 | 0 | 0 | 0 | 3 | 0 | 0 | 0 | 0 |
| 33 | POST | 1.0 | 2 | 2 | 1 | 3 | 0 | 0 | 0 | 0 |
| 34 | PRE | 5.0 | 2 | 2 | 3 | 3 | 0 | 0 | 0 | 0 |
| 34 | PRE | 1.0 | 0 | 0 | 1 | 3 | 0 | 0 | 0 | 0 |
| 34 | PRE | 0.5 | 0 | 0 | 0 | 3 | 0 | 0 | 0 | 0 |
| 34 | POST | 5.0 | 2 | 3 | 2 | 3 | 0 | 0 | 0 | 0 |
| 34 | POST | 1.0 | 2 | 1 | 2 | 3 | 0 | 0 | 0 | 0 |
| 34 | POST | 0.5 | 2 | 2 | 2 | 3 | 0 | 0 | 0 | 0 |
| 35 | PRE | 5.0 | 2 | 3 | 3 | 3 | 0 | 0 | 0 | 0 |
| 35 | PRE | 1.0 | 2 | 0 | 3 | 3 | 0 | 0 | 0 | 0 |
| 35 | POST | 5.0 | 2 | 2 | 3 | 3 | 0 | 0 | 0 | 0 |
| 35 | POST | 1.0 | 1 | 1 | 2 | 3 | 0 | 0 | 0 | 0 |
| 36 | PRE | 5.0 | 3 | 3 | 3 | 3 | 0 | 0 | 0 | 0 |
| 36 | PRE | 1.0 | 3 | 3 | 3 | 3 | 0 | 0 | 0 | 0 |
| 36 | POST | 5.0 | 3 | 3 | 3 | 3 | 0 | 0 | 0 | 0 |
| 36 | POST | 1.0 | 2 | 3 | 3 | 3 | 0 | 0 | 0 | 0 |
| 37 | PRE | 5.0 | 3 | 3 | 3 | 3 | 0 | 0 | 0 | 0 |
| 37 | PRE | 1.0 | 3 | 3 | 3 | 3 | 0 | 0 | 0 | 0 |
| 37 | POST | 5.0 | 3 | 3 | 3 | 3 | 0 | 0 | 0 | 0 |
| 37 | POST | 1.0 | 2 | 3 | 3 | 3 | 0 | 0 | 0 | 0 |
| 38 | PRE | 5.0 | 3 | 3 | 3 | 3 | 0 | 0 | 0 | 0 |
| 38 | PRE | 1.0 | 3 | 3 | 3 | 3 | 0 | 0 | 0 | 0 |
| 38 | POST | 5.0 | 3 | 3 | 3 | 3 | 0 | 0 | 0 | 0 |
| 38 | POST | 1.0 | 3 | 3 | 3 | 3 | 0 | 0 | 0 | 0 |
| 41 | PRE | 5.0 | 3 | 3 | 3 | 3 | 0 | 0 | 0 | 0 |
| 41 | PRE | 1.0 | 2 | 2 | 3 | 3 | 0 | 0 | 0 | 0 |
| 41 | POST | 5.0 | 3 | 3 | 3 | 3 | 0 | 0 | 0 | 0 |
| 41 | POST | 1.0 | 3 | 2 | 3 | 3 | 0 | 0 | 0 | 0 |
| 42 | PRE | 5.0 | 3 | 2 | 3 | 3 | 0 | 0 | 0 | 0 |
| 42 | PRE | 1.0 | 3 | 2 | 3 | 3 | 0 | 0 | 0 | 0 |
| 42 | POST | 5.0 | 2 | 2 | 3 | 3 | 0 | 0 | 0 | 0 |
| 42 | POST | 1.0 | 2 | 1 | 3 | 3 | 0 | 0 | 0 | 0 |
| 43 | PRE | 5.0 | 3 | 3 | 3 | 3 | 0 | 0 | 0 | 0 |
| 43 | PRE | 1.0 | 2 | 2 | 3 | 3 | 0 | 0 | 0 | 0 |
| 43 | POST | 5.0 | 3 | 3 | 3 | 3 | 0 | 0 | 0 | 0 |
| 43 | POST | 1.0 | 3 | 3 | 3 | 3 | 0 | 0 | 0 | 0 |
| 76 | PRE | 5.0 | 0 | 0 | 0 | 1 | 0 | 3 | 3 | 0 |
| 76 | PRE | 1.0 | 0 | 0 | 0 | 0 | 0 | 1 | 2 | — |
| 76 | POST | 5.0 | 1 | 1 | 1 | 1 | 0 | 0 | 0 | — |
| 76 | POST | 1.0 | 0 | 0 | 0 | 0 | 0 | 0 | 0 | 0 |
| 77 | PRE | 5.0 | 3 | 2 | 3 | 3 | 0 | 0 | 0 | 0 |
| 77 | PRE | 1.0 | 0 | 0 | 0 | 0 | 0 | 0 | 0 | 0 |
| 77 | POST | 5.0 | 3 | 2 | 3 | 3 | 0 | 0 | 0 | 0 |
| 77 | POST | 1.0 | 1 | 1 | 1 | 3 | 0 | 0 | 0 | 0 |
| 82 | PRE | 5.0 | 0 | 0 | 0 | 1 | 0 | 0 | 0 | 0 |
| 82 | POST | 5.0 | 2 | 0 | 2 | 3 | 2 | 2 | 3 | 3 |

The names of the test plants were as follows:
Wh Wheat
Ot Wild Oats
Rg Ryegrass
Jm Japanese millet
P Peas
IP Ipomoea
MS Mustard
Sf Sunflower

EXAMPLE 23

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 8 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as in the post-emergence test. In both cases the degree of herbicidal damage was assessed by comparison with untreated control plants. The results are given in Table 8 below. A dash (-) means that no experiment was carried out.

TABLe 8

| Compound No | APPLICATION Method Rate (kg/ha) | Sb | Rp | Ct | Sy | Mz | Ww | Rc | Sn | Ip | Am | Pi | Ca | Po | Xa | Ab | Cv | Ot | Dg | Pu | St | Ec | Sh | Ag | Cn |
|---|---|---|---|---|---|---|---|---|---|---|---|---|---|---|---|---|---|---|---|---|---|---|---|---|---|
| 1 | POST 0.1 | 1 | 0 | 0 | 2 | 3 | 2 | 2 | 1 | 0 | 1 | 0 | 1 | 0 | 0 | 0 | 0 | 2 | 4 | 0 | 4 | 4 | 4 | 2 | 0 |
| 1 | PRE 0.4 | 1 | 0 | 0 | 1 | 2 | 0 | 1 | 0 | 0 | 2 | — | 0 | 0 | 0 | 2 | — | 0 | — | 0 | 5 | 5 | 3 | 1 | 0 |
| 1 | POST 0.4 | 0 | 1 | 0 | 2 | 5 | 2 | 2 | 0 | 0 | 0 | 0 | 0 | 0 | 0 | 0 | 0 | 3 | 4 | 0 | 5 | 4 | 4 | 3 | 0 |
| 1 | PRE 0.5 | 0 | 0 | 0 | 0 | 4 | 4 | 5 | — | 3 | 0 | 5 | 0 | 0 | 0 | 1 | — | 4 | 5 | 2 | 4 | 5 | 4 | 4 | 0 |
| 1 | POST 0.5 | 0 | 0 | 0 | 0 | 5 | 3 | 3 | 0 | 0 | 0 | 0 | 0 | 0 | 0 | 0 | 0 | 4 | 4 | 1 | 4 | 5 | 3 | 0 |
| 1 | PRE 1.5 | 0 | 0 | 0 | 0 | 5 | 5 | 5 | — | 1 | 2 | 5 | 1 | 0 | 0 | 0 | — | 5 | 5 | 3 | 5 | 5 | 4 | 5 | 0 |
| 1 | POST 1.5 | 1 | 0 | 0 | 0 | 5 | 4 | 2 | 0 | 0 | 0 | 0 | 1 | 0 | 0 | 0 | — | 4 | 4 | 1 | 5 | 5 | 5 | 3 | 0 |
| 13 | PRE 0.1 | 1 | 0 | 1 | 2 | 1 | 0 | 0 | 1 | 0 | 0 | 0 | 1 | 1 | 0 | 0 | 0 | 0 | 1 | 3 | 0 | 4 | 3 | 0 | 0 |
| 13 | POST 0.1 | 0 | 0 | 0 | 0 | 3 | 2 | 2 | 1 | 0 | 1 | 0 | 0 | 0 | 0 | 0 | 0 | 1 | 3 | 0 | 3 | 3 | 1 | 0 | 0 |
| 13 | PRE 0.4 | 2 | 0 | 2 | 1 | 0 | 0 | 0 | 1 | 0 | 0 | 0 | 0 | 0 | 0 | 0. | — | 0 | 2 | 0 | 3 | 3 | 1 | 0 | 0 |
| 13 | POST 0.4 | 0 | 0 | 0 | 0 | 5 | 2 | 3 | 1 | 0 | 1 | 0 | 1 | 0 | 0 | 0 | 0 | 2 | 4 | 0 | 4 | 4 | 4 | 1 | 0 |
| 15 | PRE 0.1 | 1 | 0 | — | 0 | 0 | 0 | 0 | 2 | 0 | 0 | 0 | 0 | 1 | 0 | 0 | — | 0 | 0 | 0 | 2 | 1 | 0 | 0 | 0 |
| 15 | POST 0.1 | 0 | 0 | 0 | 0 | 3 | 2 | 2 | 0 | 0 | 0 | 0 | 0 | 0 | 2 | 0 | 0 | 2 | 3 | 0 | 4 | 5 | 3 | 1 | 0 |
| 15 | PRE 0.4 | 1 | 0 | 0 | 0 | 2 | 0 | 0 | 2 | 0 | 0 | 0 | 0 | 1 | 2 | 0 | — | 0 | 2 | 0 | 3 | 5 | 2 | 0 | 0 |
| 15 | POST 0.4 | 0 | 0 | 0 | 0 | 5 | 2 | 3 | 0 | 0 | 0 | 0 | 0 | 0 | 1 | 0 | 0 | 3 | 4 | 0 | 4 | 5 | 4 | 2 | 0 |
| 15 | PRE 0.5 | 0 | 0 | 0 | 0 | 4 | 4 | 5 | — | 0 | 1 | 4 | 0 | 0 | 4 | 1 | — | 4 | 4 | 1 | 5 | 5 | 4 | 5 | 0 |
| 15 | POST 0.5 | 2 | 0 | 0 | 0 | 5 | 3 | 3 | 0 | 0 | 0 | 0 | 0 | 0 | 0 | 0 | — | 4 | 3 | 1 | 4 | 5 | 5 | 3 | 0 |
| 15 | PRE 1.5 | 0 | 0 | 0 | 1 | 5 | 5 | 5 | — | 0 | 1 | 2 | 0 | 0 | 0 | 0 | — | 5 | 5 | 3 | 5 | 5 | 4 | 5 | 0 |
| 15 | POST 1.5 | 1 | 0 | 0 | 0 | 5 | 3 | 4 | 0 | 0 | 0 | 0 | 0 | 0 | 0 | 0 | — | 4 | 4 | 2 | 5 | 5 | 5 | 3 | 0 |
| 16 | PRE 0.1 | 2 | 0 | 0 | 0 | 0 | 0 | 0 | 0 | 0 | 0 | 1 | 2 | 1 | — | 0 | — | 0 | 0 | 0 | 1 | 0 | 0 | 0 |
| 16 | POST 0.1 | 0 | 0 | 0 | 0 | 4 | 2 | 3 | 0 | 0 | 2 | 0 | 0 | 0 | 0 | 0 | 0 | 2 | 4 | 0 | 4 | 4 | 3 | 2 | 0 |

TABLe 8-continued

| Compound No | APPLICATION Method Rate (kg/ha) | Sb | Rp | Ct | Sy | Mz | Ww | Rc | Sn | Ip | Am | Pi | Ca | Po | Xa | Ab | Cv | Ot | Dg | Pu | St | Ec | Sh | Ag | Cn |
|---|---|---|---|---|---|---|---|---|---|---|---|---|---|---|---|---|---|---|---|---|---|---|---|---|---|
| 16 | PRE 0.4 | 2 | 0 | 0 | 1 | 3 | 0 | 0 | 1 | 3 | 0 | 0 | 2 | 0 | 0 | 0 | — | 0 | 1 | 0 | 4 | 5 | 3 | 1 | 0 |
| 16 | POST 0.4 | 0 | 0 | 0 | 0 | 5 | 2 | 3 | 0 | 0 | 1 | 0 | 0 | 0 | 0 | 1 | 0 | 4 | 4 | 2 | 5 | 5 | 4 | 2 | 0 |
| 17 | PRE 0.5 | 0 | 1 | 0 | 0 | 0 | 0 | 0 | — | 3 | 0 | 5 | 0 | 0 | 0 | 1 | — | 0 | 0 | 1 | 0 | 0 | 0 | 0 | 0 |
| 17 | POST 0.5 | 0 | 0 | 0 | 0 | 0 | 0 | 0 | 1 | 0 | 0 | 0 | 0 | 0 | 1 | 0 | — | — | 0 | 0 | 0 | 0 | 0 | 0 | 0 |
| 18 | PRE 0.5 | 1 | 0 | 0 | 0 | 0 | 0 | 0 | — | 0 | 0 | — | 0 | 0 | — | 0 | — | 0 | 0 | 0 | 0 | 0 | 0 | 0 | 0 |
| 18 | POST 0.5 | 0 | 1 | 0 | 0 | 0 | 0 | 0 | 0 | 0 | 0 | 0 | 0 | 3 | 0 | 0 | — | — | 0 | 0 | 0 | 0 | 0 | 0 | 0 |
| 18 | PRE 1.5 | 0 | 0 | 2 | 0 | 0 | 0 | 0 | — | 0 | 0 | 0 | 0 | 0 | 0 | 2 | — | 0 | 0 | 0 | 0 | 0 | 0 | 0 | 0 |
| 18 | POST 1.5 | 0 | 0 | 0 | 3 | 0 | 0 | 0 | 2 | 0 | 0 | 0 | 0 | 4 | 0 | 0 | — | — | 0 | 0 | 0 | 0 | 0 | 0 | 0 |
| 20 | PRE 0.4 | 3 | 1 | 0 | 1 | 0 | 0 | 0 | 0 | 0 | 0 | 3 | 2 | 0 | 0 | 1 | — | 0 | 3 | 1 | 1 | 0 | 0 | 0 | 0 |
| 20 | POST 0.4 | 1 | 0 | 0 | 0 | 0 | 0 | 1 | 0 | 0 | 1 | 0 | 1 | 0 | 0 | 0 | 0 | 0 | 0 | 0 | 1 | 2 | 1 | 0 | 0 |
| 21 | PRE 0.4 | 2 | 0 | 1 | 0 | 1 | 0 | 0 | 0 | 0 | 1 | 0 | 2 | 0 | 0 | 0 | — | 0 | 2 | 0 | 1 | 0 | 0 | 0 | 0 |
| 21 | POST 0.4 | 1 | 0 | 0 | 0 | 4 | 1 | 2 | 0 | 0 | 1 | 0 | 2 | 0 | 0 | 1 | 0 | 0 | 4 | 0 | 4 | 4 | 4 | 1 | 0 |
| 21 | PRE 1.0 | 2 | 0 | 2 | 2 | 1 | 0 | 0 | 0 | 0 | 0 | 0 | 3 | 0 | 0 | 0 | — | 0 | 3 | 0 | 2 | 3 | 2 | 0 | 0 |
| 21 | POST 1.0 | 1 | 0 | 0 | 1 | 5 | 1 | 2 | 1 | 0 | 2 | 0 | 1 | 1 | 0 | 0 | 0 | 0 | 4 | 0 | 4 | 5 | 4 | 2 | 0 |
| 22 | PRE 0.1 | 2 | 0 | 1 | 0 | 0 | 0 | 0 | 1 | 0 | 0 | 0 | 0 | 0 | 0 | 0 | — | 0 | — | 0 | 0 | 0 | 0 | 0 | 0 |
| 22 | POST 0.1 | 0 | 0 | 0 | 0 | 0 | 0 | 0 | 0 | 0 | 1 | 0 | 1 | 0 | 0 | 0 | 0 | 0 | 0 | 0 | 0 | 0 | 0 | 0 | 0 |
| 22 | PRE 0.4 | 0 | 0 | 0 | 1 | 0 | 0 | 0 | 2 | 0 | 0 | 0 | 2 | 1 | 2 | 0 | — | 0 | 0 | 0 | 0 | 0 | 0 | 0 | 0 |
| 22 | POST 0.4 | 0 | 0 | 0 | 0 | 0 | 0 | 0 | 1 | 0 | 1 | 0 | 0 | 0 | 0 | 0 | 0 | 0 | 0 | 0 | 0 | 1 | 0 | 0 | 0 |
| 23 | PRE 1.5 | — | 0 | 0 | 0 | 0 | 0 | 0 | 1 | 0 | 2 | — | 2 | 2 | 3 | 1 | — | 0 | 0 | 0 | 0 | 0 | 0 | 0 | 1 |
| 23 | POST 1.5 | 0 | 0 | 0 | 0 | 0 | 0 | 2 | 1 | 0 | — | 0 | 1 | 0 | 0 | 1 | 0 | 0 | — | 0 | 1 | 1 | 1 | 0 | 0 |
| 23 | PRE 5.0 | 0 | 0 | 0 | 1 | 0 | 0 | 0 | 1 | 0 | 0 | 0 | 0 | 1 | 3 | 0 | — | 0 | 0 | 0 | 0 | 0 | 0 | 0 | 0 |
| 23 | POST 5.0 | 1 | 0 | 0 | 0 | 0 | 0 | 0 | 1 | 0 | — | 0 | 1 | 1 | 0 | 0 | 0 | 0 | — | 0 | 0 | 2 | 3 | 0 | 0 |
| 24 | PRE 0.5 | 0 | 0 | 0 | 0 | 0 | 0 | 0 | 1 | 0 | 0 | 1 | 0 | 0 | 2 | 0 | — | 0 | 0 | 0 | 0 | 0 | 0 | 0 | 0 |
| 24 | POST 0.5 | 0 | 0 | 0 | 0 | 0 | 0 | 2 | 1 | 0 | — | 0 | 0 | 0 | 0 | 0 | 0 | 0 | — | 0 | 0 | 1 | 1 | 0 | 0 |
| 25 | PRE 0.5 | 1 | 0 | 0 | 1 | 0 | 0 | 0 | 1 | 0 | 0 | — | 0 | 2 | — | 0 | — | 0 | 2 | 0 | 2 | 2 | 0 | 0 | 0 |
| 25 | POST 0.5 | 1 | 1 | 0 | 0 | 4 | 2 | 2 | 0 | 0 | — | 1 | 1 | 0 | 0 | 1 | 0 | 2 | — | 0 | 4 | 4 | 4 | 2 | 0 |
| 25 | PRE 1.5 | 1 | 1 | 1 | 0 | 3 | 0 | 0 | 1 | 0 | 1 | 2 | 0 | 1 | — | 1 | — | 0 | 3 | 0 | 5 | 4 | 4 | 1 | 0 |
| 25 | POST 1.5 | 1 | 0 | 0 | 0 | 4 | 3 | 3 | 1 | 0 | — | 0 | 0 | 0 | 0 | 1 | 0 | 2 | — | 0 | 5 | 5 | 3 | 3 | 0 |
| 26 | PRE 1.5 | 0 | 0 | 0 | 1 | 0 | 0 | 0 | 1 | 1 | 0 | 0 | 0 | 2 | — | 0 | — | 0 | 0 | 0 | 0 | 0 | 0 | 0 | 0 |
| 26 | POST 1.5 | 0 | 0 | 0 | 0 | 1 | 0 | 0 | 0 | 0 | — | 0 | 0 | 0 | 0 | 1 | 0 | 0 | — | 0 | 0 | 0 | 1 | 0 | 0 |
| 26 | PRE 5.0 | 1 | 0 | 2 | 1 | 0 | 0 | 0 | 1 | 0 | 0 | — | 0 | 0 | — | 0 | — | 0 | 0 | 0 | 0 | 0 | 0 | 0 | 0 |
| 26 | POST 5.0 | 0 | 1 | 0 | 0 | 0 | 0 | 0 | 1 | 0 | — | 0 | 0 | 0 | 0 | 1 | 0 | 0 | — | 0 | 0 | 0 | 1 | 0 | 0 |
| 29 | PRE 1.5 | 0 | 0 | 0 | — | 0 | 0 | 0 | 0 | — | 2 | 0 | 4 | — | 0 | 0 | — | 0 | 1 | 0 | 0 | 0 | — | 0 | 0 |
| 29 | POST 1.5 | 0 | 0 | 0 | 0 | 0 | 0 | 0 | 0 | 0 | 0 | 0 | 0 | 0 | 0 | 0 | 0 | 0 | 0 | 0 | 1 | 1 | 0 | 0 | 0 |
| 30 | PRE 1.5 | 0 | 0 | 0 | 0 | 0 | 0 | 0 | 1 | 0 | 1 | — | 0 | — | — | 0 | — | 0 | 0 | 0 | 0 | 0 | 1 | 0 | 0 |
| 30 | POST 1.5 | 0 | 0 | 0 | 0 | 0 | 0 | 0 | 0 | 0 | 0 | 0 | 0 | 0 | 0 | 0 | 0 | 0 | 0 | 0 | 1 | 1 | 0 | 0 | 0 |
| 32 | PRE 1.5 | 0 | 0 | 0 | 2 | 0 | 0 | 0 | 3 | 0 | 1 | 0 | 2 | 0 | — | 0 | — | 0 | 0 | 0 | 0 | 0 | 0 | 0 | 0 |
| 32 | POST 1.5 | 0 | 0 | 0 | 0 | 1 | 0 | 0 | 0 | 0 | 0 | 0 | 0 | 0 | 0 | 0 | 0 | 0 | 1 | 0 | 1 | 1 | 0 | 0 | 0 |
| 33 | PRE 0.5 | 0 | 0 | 0 | 0 | 0 | 0 | 0 | 1 | 0 | 0 | 0 | 2 | — | — | 0 | — | 0 | 0 | 0 | 1 | 0 | 0 | 0 | 0 |
| 33 | POST 0.5 | 0 | 0 | 0 | 0 | 2 | 2 | 3 | 1 | 0 | 0 | 0 | 0 | 0 | 0 | 0 | 0 | 1 | 4 | 0 | 4 | 4 | 2 | 2 | 0 |
| 33 | PRE 1.5 | 0 | 0 | 0 | 0 | 2 | 2 | 3 | 0 | 0 | 0 | 0 | 0 | — | 0 | 0 | — | 0 | 0 | 0 | 4 | 4 | 0 | 1 | 0 |
| 33 | POST 1.5 | 1 | 1 | 0 | 0 | 4 | 2 | 2 | 0 | 0 | 0 | 0 | 1 | 0 | 0 | 0 | 0 | 2 | 4 | 0 | 4 | 4 | 3 | 2 | 0 |
| 34 | PRE 0.5 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 |
| 34 | POST 0.5 | 0 | 0 | 0 | 0 | 3 | 0 | 1 | 0 | 0 | 1 | 0 | 0 | 0 | 0 | 0 | 0 | 0 | 3 | 0 | 3 | 3 | 2 | 0 | 0 |
| 34 | PRE 1.5 | 0 | 0 | 0 | 0 | 0 | 0 | 0 | 0 | 0 | 2 | 0 | 0 | 0 | 0 | 0 | — | 0 | 1 | 0 | 3 | 2 | 0 | 0 | 0 |
| 34 | POST 1.5 | 3 | 0 | 0 | 0 | 4 | 1 | 2 | 0 | 0 | 0 | 0 | 0 | 0 | 0 | 0 | 0 | 0 | 4 | 0 | 4 | 5 | 2 | 1 | 0 |
| 35 | PRE 0.5 | 1 | 0 | 0 | — | 0 | 0 | 0 | — | 0 | 1 | 0 | 0 | 0 | 0 | 0 | — | 0 | 0 | 1 | 0 | 0 | 0 | 0 | 0 |
| 35 | POST 0.5 | 0 | 0 | 0 | 0 | 3 | 0 | 1 | 0 | 0 | 0 | 0 | 0 | 0 | 0 | 0 | 1 | 0 | 2 | 0 | 4 | 4 | 1 | 0 | 0 |
| 35 | PRE 1.5 | 0 | 0 | 0 | 0 | 1 | 0 | 2 | 0 | 0 | 1 | 0 | 0 | 0 | 0 | 0 | — | 0 | 0 | 0 | 4 | 3 | 0 | 0 | 0 |
| 35 | POST 1.5 | 0 | 0 | 0 | 0 | 4 | 1 | 3 | 0 | 0 | 2 | 0 | 0 | 0 | 0 | 0 | 0 | 1 | 4 | 0 | 4 | 4 | 4 | 0 | 0 |
| 73 | PRE 0.5 | 0 | 0 | — | 0 | 4 | 3 | 5 | — | 0 | 0 | 0 | 0 | — | 0 | 0 | 0 | — | 1 | 4 | 0 | 4 | 3 | 0 | 0 |
| 73 | POST 0.5 | 0 | 0 | 0 | 0 | 5 | 3 | 4 | 0 | 0 | — | 0 | 0 | 2 | — | 0 | 0 | 0 | 4 | 0 | 0 | 1 | 0 | 0 | 0 |
| 73 | PRE 1.5 | 0 | 0 | 0 | 0 | 4 | 3 | 5 | 0 | 0 | 0 | 0 | 0 | 0 | 0 | 0 | — | 4 | 4 | 1 | 4 | 5 | 4 | 4 | 0 |
| 73 | POST 1.5 | 0 | 0 | 0 | 0 | 5 | 4 | 4 | 0 | 0 | 1 | 0 | 1 | 0 | 0 | 0 | 0 | 5 | 5 | 3 | 5 | 5 | 5 | 3 | 0 |
| 74 | PRE 0.5 | 0 | 0 | 0 | 0 | 5 | 2 | 2 | — | 0 | 1 | 0 | 0 | — | 0 | 0 | 0 | 3 | 4 | 0 | 5 | 4 | 1 | 2 | 0 |
| 74 | POST 0.5 | 0 | 0 | 0 | 0 | 5 | 3 | 4 | 0 | 0 | 0 | 0 | 0 | 0 | — | 0 | 0 | 4 | 5 | 2 | 5 | 5 | 4 | 3 | 0 |
| 74 | PRE 1.5 | 0 | 0 | 0 | 0 | 5 | 5 | 5 | 0 | 0 | 3 | 0 | 0 | — | — | 0 | — | 5 | 4 | 2 | 5 | 5 | 4 | 4 | 0 |
| 74 | POST 1.5 | 0 | 0 | 0 | 0 | 5 | 4 | 4 | 0 | 0 | 0 | 0 | 0 | 0 | 0 | 0 | 0 | 5 | 5 | 3 | 5 | 5 | 5 | 3 | 0 |
| 75 | PRE 0.5 | 0 | 0 | 0 | 0 | 5 | 1 | 5 | 0 | 0 | 0 | 0 | — | 0 | — | 0 | 2 | — | 1 | 4 | 0 | 4 | 3 | 2 | 0 | 0 |
| 75 | POST 0.5 | 0 | 0 | 0 | 0 | 5 | 3 | 3 | 1 | 0 | 0 | 0 | 0 | 0 | 0 | 0 | 0 | 4 | 5 | 2 | 5 | 5 | 4 | 3 | 0 |
| 75 | PRE 1.5 | 0 | 0 | 0 | 0 | 5 | 4 | 5 | 0 | 0 | 2 | 0 | 0 | 1 | — | 2 | — | 5 | 4 | 0 | 5 | 5 | 5 | 3 | 0 |
| 75 | POST 1.5 | 0 | 0 | 0 | 0 | 5 | 4 | 4 | 0 | 0 | 0 | 0 | 1 | 0 | 0 | 0 | 0 | 4 | 5 | 3 | 5 | 5 | 5 | 3 | 0 |
| 78 | PRE 1.0 | 0 | 0 | 1 | 0 | 0 | 0 | 0 | — | 0 | 0 | 0 | 0 | 1 | 0 | 1 | — | 0 | — | 0 | 0 | 0 | 0 | 0 | 0 |
| 78 | POST 1.0 | 2 | 1 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| 78 | PRE 5.0 | 2 | 0 | 1 | 0 | 0 | 0 | 0 | — | 0 | 0 | 0 | 0 | 2 | 0 | 0 | — | 0 | — | 0 | 0 | 0 | 0 | 0 | 0 |
| 78 | POST 5.0 | 2 | 2 | 1 | 2 | 0 | 0 | 0 | 0 | 0 | 1 | 0 | 4 | 0 | 0 | 1 | — | 0 | 0 | 0 | 0 | 0 | 0 | 0 | 0 |
| 79 | PRE 5.0 | 2 | 0 | 0 | 0 | 0 | 0 | 0 | 3 | 0 | 0 | — | 0 | 1 | 0 | 2 | — | 0 | 0 | 0 | 0 | 0 | 0 | 0 | 0 |
| 79 | POST 5.0 | 1 | 2 | 0 | 0 | 0 | 0 | 0 | 0 | 0 | — | 0 | 0 | 2 | — | 0 | 0 | 0 | 0 | 4 | 0 | 0 | 1 | 0 | 0 |
| 80 | PRE 0.5 | 1 | 0 | 0 | 0 | 1 | 0 | 0 | 1 | 0 | 1 | 0 | 2 | 0 | 0 | 0 | — | 0 | 3 | 0 | 4 | 0 | 0 | 0 | 0 |
| 80 | POST 0.5 | 0 | 0 | 0 | 0 | 4 | 2 | 3 | 0 | 1 | 0 | 0 | 1 | 0 | 0 | 0 | 0 | 3 | 4 | 0 | 4 | 5 | 3 | 2 | 0 |
| 80 | PRE 1.5 | 1 | 0 | 0 | — | 4 | 3 | 1 | 1 | 0 | 1 | 0 | 2 | — | — | 0 | — | 4 | 4 | 0 | 4 | 5 | 0 | 2 | 0 |
| 80 | POST 1.5 | 0 | 0 | 0 | 0 | 5 | 3 | 3 | 0 | 1 | 0 | 1 | 0 | 0 | 0 | 0 | 0 | 4 | 5 | 1 | 5 | 5 | 4 | 2 | 0 |
| 87 | PRE 0.1 | 1 | 0 | 1 | 0 | 0 | 0 | 0 | 0 | 0 | 0 | 0 | 3 | 0 | 0 | 0 | — | 0 | 3 | 0 | 0 | 0 | 0 | 0 | 0 |
| 87 | POST 0.1 | 0 | 0 | 0 | 0 | 0 | 0 | 0 | 1 | 0 | 1 | 0 | 0 | 0 | 0 | 0 | 0 | 0 | 0 | 0 | 0 | 0 | 0 | 0 | 0 |
| 87 | PRE 0.4 | 0 | 0 | 2 | 2 | 0 | 0 | 0 | 2 | 0 | 0 | 1 | 2 | 0 | 0 | 0 | — | 0 | 3 | 0 | 0 | 1 | 0 | 0 | 0 |

TABLe 8-continued

| Compound No | APPLICATION Method Rate (kg/ha) | TEST PLANTS |||||||||||||||||||||||
|---|---|---|---|---|---|---|---|---|---|---|---|---|---|---|---|---|---|---|---|---|---|---|---|---|
| | | Sb | Rp | Ct | Sy | Mz | Ww | Rc | Sn | Ip | Am | Pi | Ca | Po | Xa | Ab | Cv | Ot | Dg | Pu | St | Ec | Sh | Ag | Cn |
| 87 | POST 0.4 | 1 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 |

The names of the test plants were as follows:
Sb Sugar beet
Rp Rape
Ct Cotton
Sy Soya bean
Mz Maize
Ww Winter wheat
Rc Rice
Sn *Senecio vulgaris*
Ip *Ipomoea purpurea*
Am *Amaranthus retroflexus*
Pi *Polygonum aviculare*
Ca *Chenopodium album*
Po *Portulaca oleracea*
Xa *Xanthium pensylvanicum*
Ab *Abutilon theophrastii*
Cv *Convolvulus arvensis*
Ot Cultivated oats and wild oats (*Avena fatua*) Wild oats are used in the post-emergence test and cultivated oats in the pre-emergence test
Dg *Digitaria sanguinalis*
Pu *Poa annua*
St *Setaria viridis*
Ec *Echinochloa crus-galli*
Sh *Sorghum halepense*
Ag *Agropyron repens*
Cn *Cyperus rotundus*

EXAMPLE 24

This Example illustrates the selective herbicidal activity of compounds of the invention.

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml of water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 9 below. Damage to test plants was assessed after 14 days on a scale of 0 to 9 where 0 to 10% damage and 9 is complete kill. The degree of herbicidal damage was assessed by comparison with untreated control plants and the results are given in Table 9 below. A dash (-) means that no experiment was carried out.

TABLE 9

| | CROPS ||| | WEEDS ||||
|---|---|---|---|---|---|---|---|---|
| Compound No | Application Rate (kg/ha) | Sy | Ct | Sb | Application Rate (kg/ha) | Ec | Dg | Av | Al |
| 62 | 0.5 | 0 | 0 | 0 | 0.05 | 4 | 0 | 0 | 0 |
| | 0.75 | 0 | 0 | 0 | 0.075 | 6 | 2 | 1 | 0 |
| | 1.0 | 0 | 0 | 0 | 0.1 | 8 | 5 | 1 | 2 |
| | 1.5 | 0 | 0 | 0 | 0.15 | 9 | 6 | 2 | 0 |
| 15 | 0.5 | 0 | 0 | 0 | 0.05 | 7 | 6 | 2 | 0 |
| | 0.75 | 0 | 0 | 0 | 0.075 | 9 | 7 | 4 | 0 |
| | 1.0 | 0 | 0 | 0 | 0.1 | 9 | 8 | 4 | 2 |
| | 1.5 | 0 | 0 | 0 | 0.15 | 9 | 9 | 6 | 6 |
| 1 | 0.5 | 0 | 0 | 0 | 0.05 | 9 | 4 | 1 | 0 |
| | 0.75 | 0 | 0 | 0 | 0.075 | 9 | 6 | 4 | 0 |
| | 1.0 | 0 | 0 | 0 | 0.1 | 9 | 8 | 4 | 1 |
| | 1.5 | 0 | 0 | 0 | 0.15 | 9 | 9 | 6 | 1 |
| 63 | 0.5 | 0 | 0 | 0 | 0.05 | 9 | 2 | 2 | 0 |
| | 0.75 | 0 | 0 | 0 | 0.075 | 9 | 5 | 3 | 0 |
| | 1.0 | 0 | 0 | 0 | 0.1 | 9 | 8 | 6 | 3 |
| | 1.5 | 0 | 0 | 0 | 0.15 | 9 | 9 | 7 | 3 |
| 64 | 0.5 | 0 | 0 | 0 | 0.05 | 9 | 3 | 2 | 0 |
| | 0.75 | 0 | 0 | 0 | 0.075 | 9 | 7 | 3 | 4 |
| | 1.0 | 0 | 0 | 0 | 0.1 | 9 | 9 | 5 | 2 |
| | 1.5 | 0 | 0 | 0 | 0.15 | 9 | 9 | 7 | 6 |
| 28 | 0.5 | 0 | 0 | 0 | 0.05 | 9 | 2 | 2 | 1 |
| | 0.75 | 0 | 0 | 0 | 0.075 | 9 | 5 | 3 | 4 |
| | 1.0 | 0 | 0 | 0 | 0.1 | 9 | 6 | 5 | 2 |
| | 1.5 | 0 | 0 | 0 | 0.15 | 9 | 9 | 6 | 5 |
| 66 | 0.5 | 0 | 0 | 0 | 0.05 | 9 | 3 | 1 | 0 |
| | 0.75 | 0 | 0 | 0 | 0.075 | 9 | 5 | 2 | 1 |
| | 1.0 | 0 | 0 | 0 | 0.1 | 9 | 9 | 4 | 2 |
| | 1.5 | 0 | 0 | 0 | 0.15 | 9 | 9 | 6 | 1 |
| 65 | 0.5 | 0 | 0 | 0 | 0.05 | 8 | 5 | 2 | 1 |
| | 0.75 | 0 | 0 | 0 | 0.075 | 9 | 6 | 4 | 1 |
| | 1.0 | 0 | 0 | 0 | 0.1 | 9 | 8 | 5 | 2 |
| | 1.5 | 0 | 0 | 0 | 0.15 | 9 | 9 | 6 | 6 |
| 67 | 0.5 | 0 | 0 | 0 | 0.05 | 8 | 4 | 3 | 0 |
| | 0.75 | 0 | 0 | 0 | 0.075 | 9 | 5 | 2 | 1 |
| | 1.0 | 0 | 0 | 0 | 0.1 | 9 | 7 | 5 | 1 |
| | 1.5 | 0 | 0 | 0 | 0.15 | 9 | 9 | 7 | 6 |
| 68 | 0.5 | 0 | 0 | 0 | 0.05 | 8 | 1 | 1 | 0 |
| | 0.75 | 0 | 0 | 0 | 0.075 | 9 | 3 | 2 | 1 |
| | 1.0 | 0 | 0 | 0 | 0.1 | 9 | 6 | 3 | 1 |
| | 1.5 | 0 | 0 | 0 | 0.15 | 9 | 8 | 5 | 2 |
| 69 | 0.5 | 0 | 0 | 0 | 0.05 | 7 | 2 | 1 | 0 |
| | 0.75 | 0 | 0 | 0 | 0.075 | 9 | 4 | 3 | 1 |
| | 1.0 | 0 | 0 | 0 | 0.1 | 9 | 6 | 4 | 1 |
| | 1.2 | 0 | 0 | 0 | 0.15 | 9 | 8 | 6 | 3 |
| 70 | 0.5 | 0 | 0 | 0 | 0.05 | 8 | 2 | 1 | 0 |
| | 0.75 | 0 | 0 | 0 | 0.075 | 9 | 4 | 2 | 1 |
| | 1.0 | 0 | 0 | 0 | 0.1 | 9 | 7 | 4 | 2 |
| | 1.5 | 0 | 0 | 0 | 0.15 | 9 | 9 | 6 | 5 |
| 71 | 0.5 | 0 | 0 | 0 | 0.05 | 7 | 3 | 3 | 0 |
| | 0.75 | 0 | 0 | 0 | 0.075 | 9 | 6 | 3 | 0 |
| | 0.9 | 0 | 0 | 0 | 0.1 | 9 | 7 | 3 | 2 |
| | 1.1 | 0 | 0 | 0 | 0.15 | 9 | 9 | 6 | 4 |
| 72 | 0.5 | 0 | 0 | 0 | 0.05 | 8 | 4 | 2 | 0 |
| | 0.75 | 0 | 0 | 0 | 0.075 | 9 | 4 | 4 | 0 |
| | 1.0 | 0 | 0 | 0 | 0.1 | 9 | 5 | 5 | 2 |

TABLE 9-continued

| Com-pound No | Application Rate (kg/ha) | CROPS | | | Application Rate (kg/ha) | WEEDS | | | |
|---|---|---|---|---|---|---|---|---|---|
| | | Sy | Ct | Sb | | Ec | Dg | Av | Al |
| | 1.5 | 0 | 0 | 0 | 0.15 | 9 | 6 | 6 | 3 |

The names of the test plants were as follows:
Sy Soya bean
Ct Cotton
Sb Sugar beet
Ec *Echinochloa crus-galli*
Dg *Digitaria sanguinalis*
Av *Avena fatua*
Al *Alopecurus myosuroides*

EXAMPLE 25

This Example illustrates the selective herbicidal activity of compounds of the invention when applied postemergence in the field.

The test compounds were formulated following essentially the same procedure described in Example 24.

The test plant species were sown on flat-topped hills spaced 1 meter apart using a Stanhay Precision Seeder, two species being sown on each hill. The species were planted at different times so that they would all reach approximately the same stage of growth at the time of spraying. The flat-topped hills on which the plant species were sown were grouped in main-plots on the basis of the test compound and sub-plots of the main-plot on the basis of rate of application of the test chemical.

Each flat-topped hill was pegged to a 1.25 meter centre and sprayed with the appropriate formulated test-compound to a width of 1 meter using an Oxford Precision Sprayer fitted with two No "0" T-jets.

Each test had two replicates and the damage to the test plants was visually assessed 23 days after spraying. The results, expressed as percentage kill, are given in Table 10 below.

TABLE 10

| Compound No | Application Rate (kg/ha) | TEST PLANTS | | | | | | |
|---|---|---|---|---|---|---|---|---|
| | | MONOCOTYLEDONS | | | DICOTYLEDONS | | | |
| | | Mz | Sg | Ec | Sr | Ct | Sy | Pn |
| 14 | 0 | 5.0 | 0.0 | 5.0 | 0.0 | 0.0 | 0.0 | 2.5 |
| 14 | 0.5 | 12.5 | 35.0 | 50.0 | 0.0 | 5.0 | 0.0 | 2.5 |
| 14 | 1.0 | 95.0 | 92.5 | 90.0 | 0.0 | 2.5 | 2.5 | 10.0 |
| 14 | 2.0 | 87.5 | 87.5 | 90.0 | 0.0 | 0.0 | 0.0 | 0.0 |
| 15 | 0 | 5.0 | 0.0 | 17.5 | 0.0 | 5.0 | 0.0 | 0.0 |
| 15 | 0.5 | 50.0 | 72.5 | 60.0 | 0.0 | 0.0 | 0.0 | 0.0 |
| 15 | 1.0 | 85.0 | 85.0 | 92.5 | 0.0 | 0.0 | 0.0 | 0.0 |
| 15 | 2.0 | 100.0 | 100.0 | 97.5 | 0.0 | 0.0 | 0.0 | 0.0 |
| 28 | 0 | 5.0 | 0.0 | 0.0 | 0.0 | 0.0 | 0.0 | 7.5 |
| 28 | 0.5 | 52.5 | 72.5 | 67.5 | 0.0 | 0.0 | 0.0 | 0.0 |
| 28 | 1.0 | 92.5 | 90.0 | 92.5 | 0.0 | 0.0 | 0.0 | 2.5 |
| 28 | 2.0 | 100.0 | 97.5 | 99.0 | 0.0 | 0.0 | 0.0 | 0.0 |

The names of the test plants and their growth stage at spraying are as follows:

| Code | Species | Variety | Growth Stage at Spraying |
|---|---|---|---|
| Mz | Maize | XL361 | 2-3 leaf |
| Sq | Sorghum | NK207 | 2-3 leaf |
| Ec | *Echinochloa* | crus-galli* | 3-4 leaf |
| Sr | Sunflower | sunfola | 2-3 leaf |
| Ct | Cotton | Delta Pine | 1-2 leaf |
| Sy | Soya bean | Clarke 63 | 2-3 leaf |
| Pn | Peanut | Red Spanish | 2 leaf |

*Volunteer species (not shown).

We claim:
1. A compound of the formula:

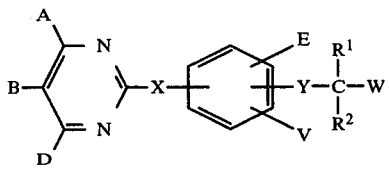

wherein:
A, B and D are independently chosen from the group consisting of hydrogen, halogen, $C_1$ to $C_6$ alkyl, $C_1$ to $C_6$ haloalkyl, $C_1$ to $C_6$ (alkoxy) carbonyl, amino, $C_1$ to $C_6$ alkylamino, di($C_1$ to $C_6$ alkyl) amino, cyano, phenyl, phenoxy, halophenyl, halophenoxy, nitrophenyl and nitrophenoxy;

E and V are independently chosen from the group consisting of hydrogen, halogen, nitro, $C_1$ to $C_6$ alkyl and $C_1$ to $C_6$ haloalkyl;

$R^1$ and $R^2$ are independently chosen from hydrogen $C_1$ to $C_6$ alkyl;

W is the group

wherein G is chosen from the group consisting of hydroxy, mercapto, $C_1$ to $C_{10}$ alkoxy, $C_1$ to $C_{10}$ haloalkoxy, $C_1$ to $C_{10}$ alkoxy substituted with $C_1$ to $C_6$ alkoxy, $C_1$ to $C_{10}$ alkylthio, $C_2$ to $C_{10}$ alkenyloxy, $C_2$ to $C_{10}$ alkenylthio, $C_2$ to $C_{10}$ alkynyloxy, $C_3$ to $C_7$ cycloalkoxy, phenoxy, benzyloxy, nitrophenoxy, halophenoxy, nitrobenzyloxy, halobenzyloxy, phenylthio, benzylthio, amino, $C_1$ to $C_6$ alkylamino, di($C_1$ to $C_6$ alkyl)amino, thenylamino, anilino, morpholino and the group OM wherein M is an alkali metal ion or alkaline earth metal ion;

X is chosen from oxygen and sulfur; and
Y is oxygen.

2. A compound according to claim 1 wherein the phenyl ring

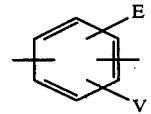

is substituted in the 1-position by the group

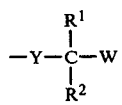

and in the 4-position by the group

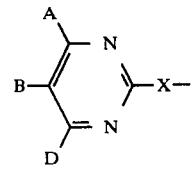

to give a compound of formula XX

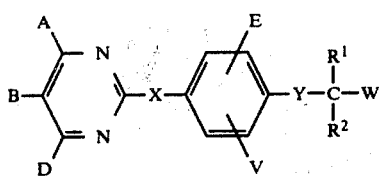

XX.

3. A compound according to claim 1 wherein the phenyl ring

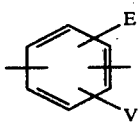

is substituted in the 1-position by the group

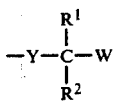

and in the 3-position by the group

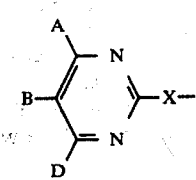

to give a compound of formula XXI

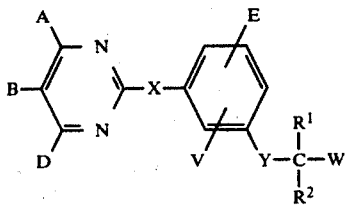

XXI.

4. A compound according to claim 1 wherein the phenyl ring

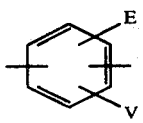

is substituted in the 1-position by the group

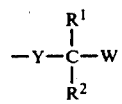

and in the 2-position by the group

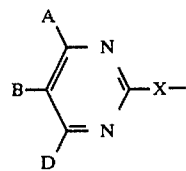

to give a compound of formula XXII

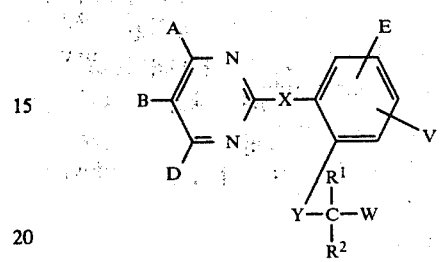

XXII.

5. A compound according to claim 1 wherein X and Y are both oxygen.

6. A compound according to claim 5 wherein:
V is hydrogen;
A and D are chosen from hydrogen, $C_1$ to $C_6$ alkyl, $C_1$ to $C_6$ alkoxycarbonyl and halogen;
B is chosen from halogen, cyano, $C_1$ to $C_6$ alkoxycarbonyl, $C_1$ to $C_6$ alkyl, $C_1$ to $C_6$ alkoxy, trifluoromethyl, phenyl optionally substituted with halogen or nitro and phenoxy optionally substituted with halogen;
E is chosen from hydrogen, halogen, nitro, trifluoromethyl and $C_1$ to $C_6$ alkyl;
$R^1$ is chosen from hydrogen and $C_1$ to $C_6$ alkyl;
$R^2$ is hydrogen or methyl; and
W is the group

wherein G is chosen from the group consisting of hydroxy, $C_1$ to $C_{10}$ alkoxy, $C_1$ to $C_{10}$ haloalkoxy, $C_1$ to $C_{10}$ alkylthio, $C_2$ to $C_{10}$ alkenyloxy, $C_2$ to $C_{10}$ alkynyloxy, cyclohexyloxy, phenoxy, nitrophenoxy, benzyloxy, benzylthio, di-($C_1$ to $C_6$ alkyl)amino, thenylamino, anilino and morpholino.

7. A compound according to claim 6 wherein:
A, D, V and $R^2$ are hydrogen; X and Y are both oxygen; B is chosen from halogen and trifluoromethyl; E is chosen from hydrogen, halogen nitro, trifluoromethyl, and $C_1$ to $C_6$ alkyl;
$R^1$ is chosen from $C_1$ to $C_6$ alkyl; and W is the group

wherein G is chosen from the group consisting of hydroxy, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy and cyclohexyloxy.

8. A compound according to claim 7 wherein:
A, D, E, V and $R^2$ are hydrogen; X and Y are both oxygen;
B is chosen from halogen and trifluoromethyl;

R¹ is methyl; and
W is the group

wherein G is chosen from the group consisting of methoxy, ethoxy, n-propoxy, isopropoxy, n-butoxy, 2-methylpropoxy, 1-methylpropoxy, N-pentyloxy, 1,3-dimethylbutoxy, 2-ethylhexyloxy, n-octyloxy, cyclohexyloxy, 1-methyl-1-trichloromethylethoxy, allyloxy, 2-propynyloxy and 2-methoxyethoxy.

9. The compound

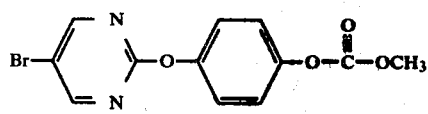

10. The compound

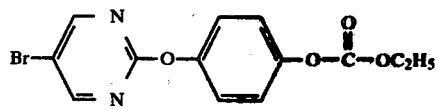

11. The compound

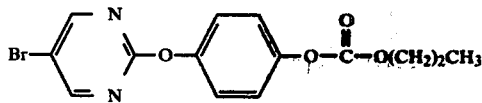

12. The compound

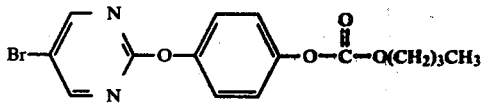

13. The compound

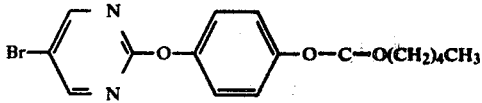

14. The compound

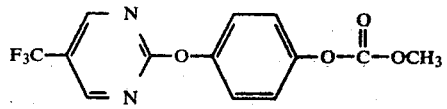

15. The compound

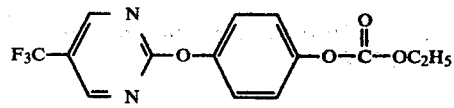

16. The compound

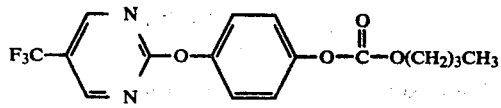

17. A process of severely damaging or killing unwanted plants which process comprises applying to the plants, or to the growth medium of the plants, an effective amount of a compound as defined according to claim 1.

18. A process of selectively controlling the growth of weeds in crops which process comprises applying to the crop, or to the growth medium of the crop, a compound as defined according to claim 1 in an amount sufficient to severely damage or kill the weeds but insufficient to damage the crop substantially.

19. A process according to claim 18 wherein the crops are dicotyledonous and the weeds are monocotyledonous.

20. A process according to claim 18 wherein the crops are cereal crops.

21. A process according to claim 17 wherein the compound is applied at a rate in the range from 0.01 to 20 kilograms per hectare.

22. A process according to claim 21 wherein the rate is in the range from 0.1 to 2 kilograms per hectare.

23. A herbicidal composition comprising as active ingredient a compound as defined according to claim 1 and a carrier therefor.

24. A composition according to claim 23 wherein the composition is in the form of a liquid and comprises a surface active agent.

25. A composition according to claim 23 wherein the composition is in the form of a powder.

26. A dilute composition according to claim 23 which comprises from 0.01 to 2% by weight of active ingredient.

27. A concentrated composition according to claim 23 which comprises from 20 to 90% by weight of active ingredient.

28. The compound

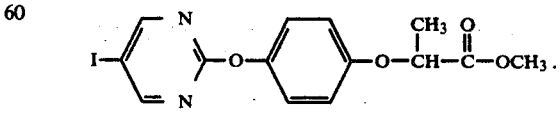

* * * * *